(12) United States Patent
Qin et al.

(10) Patent No.: US 8,916,012 B2
(45) Date of Patent: Dec. 23, 2014

(54) METHOD OF MAKING SUBSTRATES COMPRISING FROTHED BENEFIT AGENTS

(75) Inventors: Jian Qin, Appleton, WI (US); Deborah J. Calewarts, Appleton, WI (US); Jeffrey F. Jurena, Appleton, WI (US); Keyur M. Desai, Atlanta, GA (US); Donald E. Waldroup, Roswell, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 297 days.

(21) Appl. No.: 13/330,440

(22) Filed: Dec. 19, 2011

(65) Prior Publication Data

US 2012/0164200 A1 Jun. 28, 2012

Related U.S. Application Data

(63) Continuation-in-part of application No. 12/979,852, filed on Dec. 28, 2010.

(51) Int. Cl.
| | |
|---|---|
| *A61K 8/04* | (2006.01) |
| *B32B 5/24* | (2006.01) |
| *B32B 5/20* | (2006.01) |
| *A61K 8/02* | (2006.01) |
| *B32B 5/02* | (2006.01) |

(52) U.S. Cl.
CPC .................. *B32B 5/245* (2013.01); *A61K 8/046* (2013.01); *A61K 2800/412* (2013.01); *B32B 5/20* (2013.01); *B32B 2555/02* (2013.01); *A61K 8/025* (2013.01); *B32B 5/022* (2013.01); *A61K 8/027* (2013.01); *A61K 8/0208* (2013.01)
USPC .......................................... 156/231; 156/247

(58) Field of Classification Search
None
See application file for complete search history.

(56) References Cited

U.S. PATENT DOCUMENTS

| | | | |
|---|---|---|---|
| 2,897,109 | A | 7/1959 | Voigtman |
| 3,188,372 | A | 6/1965 | Roos |
| 3,484,839 | A | 12/1969 | Neumann |
| 3,810,280 | A | 5/1974 | Munchbach et al. |
| 3,865,078 | A | 2/1975 | De Howitt et al. |
| 3,926,716 | A | 12/1975 | Bates |
| 4,237,818 | A | 12/1980 | Clifford et al. |

(Continued)

FOREIGN PATENT DOCUMENTS

| | | |
|---|---|---|
| DE | 2 063 961 A1 | 7/1972 |
| EP | 1 619 016 A1 | 1/2006 |

(Continued)

OTHER PUBLICATIONS

Co-pending U.S. Appl. No. 13/330,504, filed Dec. 19, 2011, by Jackson et al. for "Nonwoven Composite Including Regenerated Cellulose Fibers."

*Primary Examiner* — Barbara J Musser
(74) *Attorney, Agent, or Firm* — Denise L. Stoker; Kenya T. Pierre

(57) ABSTRACT

The present invention provides a nonwoven substrate comprising a fibrous web defining a surface; and a layer of a benefit agent wherein said benefit agent is selected from an additive composition, an enhancement component and combinations thereof; wherein said benefit agent is frothed and bonded to the fibrous web surface through a creping process. Additionally, the present invention provides for a method of creping a nonwoven substrate and also provides for a nonwoven substrate comprising an adhesive film of an aqueous, frothed, benefit agent.

6 Claims, 15 Drawing Sheets

(56) References Cited

U.S. PATENT DOCUMENTS

| | | |
|---|---|---|
| 4,276,339 A | 6/1981 | Stoveken |
| 4,353,993 A | 10/1982 | McCrossin |
| 4,364,784 A | 12/1982 | Van Wersch et al. |
| 4,402,200 A | 9/1983 | Clifford et al. |
| 4,448,818 A | 5/1984 | Hartog et al. |
| 4,483,894 A | 11/1984 | Porter et al. |
| 4,620,983 A | 11/1986 | Zimmer |
| 4,655,056 A | 4/1987 | Zeiffer |
| 5,429,840 A | 7/1995 | Raterman et al. |
| 5,494,744 A | 2/1996 | Everhart et al. |
| 5,611,890 A | 3/1997 | Vinson |
| 5,700,352 A | 12/1997 | Vinson |
| 5,704,101 A | 1/1998 | Majors et al. |
| 5,843,058 A | 12/1998 | Quist |
| 5,942,085 A | 8/1999 | Neal et al. |
| 6,187,138 B1 | 2/2001 | Neal et al. |
| 6,241,713 B1 | 6/2001 | Gross et al. |
| 6,261,679 B1 | 7/2001 | Chen et al. |
| 6,395,088 B1 | 5/2002 | Zeiffer |
| 6,511,734 B1 | 1/2003 | Wagner |
| 6,582,555 B2 | 6/2003 | Capizzi et al. |
| 6,585,855 B2 | 7/2003 | Drew |
| 6,623,837 B2 | 9/2003 | Morman et al. |
| 6,632,974 B1 | 10/2003 | Suzuki et al. |
| 6,642,430 B1 | 11/2003 | Busam et al. |
| 6,730,171 B2 | 5/2004 | Capizzi et al. |
| 6,752,907 B2 | 6/2004 | Edwards |
| 6,761,800 B2 | 7/2004 | Capizzi |
| 6,797,116 B2 | 9/2004 | Capizzi |
| 6,797,319 B2 | 9/2004 | Capizzi |
| 6,814,806 B2 | 11/2004 | Zeiffer et al. |
| 6,835,418 B2 | 12/2004 | Capizzi |
| 6,852,196 B2 | 2/2005 | Capizzi |
| 6,858,256 B2 | 2/2005 | Zeiffer |
| 7,431,771 B2 | 10/2008 | Zeiffer et al. |
| 7,439,276 B2 | 10/2008 | Strandburg et al. |
| 7,528,080 B2 | 5/2009 | Prieto et al. |
| 7,812,062 B2 | 10/2010 | Strandburg et al. |
| 8,012,285 B2 | 9/2011 | Goldstein et al. |
| 8,063,128 B2 | 11/2011 | Moncla et al. |
| 2005/0136242 A1 | 6/2005 | Yahiaoui et al. |
| 2006/0102071 A1 | 5/2006 | Zeiffer et al. |
| 2006/0189240 A1 | 8/2006 | Taylor et al. |
| 2008/0076844 A1 | 3/2008 | Van Sumeren et al. |
| 2008/0128101 A1* | 6/2008 | Furman et al. ................ 162/158 |
| 2008/0176968 A1 | 7/2008 | Van Sumeren et al. |
| 2008/0200891 A1 | 8/2008 | Kim et al. |
| 2008/0295985 A1 | 12/2008 | Moncla et al. |
| 2009/0088037 A1 | 4/2009 | Covelli et al. |
| 2010/0036024 A1 | 2/2010 | Menning |
| 2010/0155004 A1 | 6/2010 | Soerens et al. |
| 2010/0159200 A1 | 6/2010 | Soerens et al. |
| 2010/0227520 A1 | 9/2010 | Claasen et al. |
| 2012/0028004 A1 | 2/2012 | Qin et al. |

FOREIGN PATENT DOCUMENTS

| | | |
|---|---|---|
| GB | 758 745 A | 10/1956 |
| GB | 934 071 A | 8/1963 |
| JP | 04-135675 A | 5/1992 |
| JP | 2005-193693 A | 7/2005 |
| WO | WO 94/22502 A1 | 10/1994 |
| WO | WO 00/07045 A1 | 2/2000 |
| WO | WO 2004/069424 A2 | 8/2004 |
| WO | WO 2009/045731 A3 | 7/2009 |
| WO | WO 2012/015624 A1 | 2/2012 |

* cited by examiner

METHOD OF MAKING SUBSTRATES COMPRISING FROTHED BENEFIT AGENTS

CROSS REFERENCE TO RELATED APPLICATION

This application is a continuation-in-part of U.S. patent application Ser. No. 12/979,852 filed Dec. 28, 2010, the entirety of which is incorporated by reference herein.

FIELD OF THE INVENTION

The present invention relates to a creped nonwoven substrate comprising a frothed polymer and additional softness enhancers and the method of making the same.

BACKGROUND OF THE INVENTION

Absorbent nonwoven products such as paper towels, tissues, diapers, and other similar products are designed to have desired levels of bulk, softness and strength. For example, in some tissue products, softness is enhanced by a topical additive composition such as a softening agent to the outer surface(s) of a tissue web. Such additive composition may be a bonding agent that is topically applied to a substrate, such as a nonwoven, alone or in combination with creping operations. Creping may be part of a nonwoven manufacturing process wherein tissue is adhered to the hot surface of a rotating dryer drum by an additive composition. The dried tissue and additive composition are together scraped off the dryer drum via a doctor blade assembly. Creping adds bulk to tissue base sheets which in turn, increases softness as determined by hand feel. Other properties are affected as well, such as strength, flexibility, crepe folds and the like. Typically, additive compositions may be sprayed onto the dryer drum of a Yankee dryer. However, the spraying process has low chemical mass efficiency levels (40% to 70%) due to waste of the additive composition caused by a boundary layer of air near the dryer's surface and relatively high dryer temperatures. By necessity, the applicator is typically about 4 inches (101.6 mm) away from the dryer surface. Due to the high rotational speed of the dryer, the boundary layer of air near the dryer surface is pulled along creating a pressure barrier that inhibits spray particles from reaching the dryer surface.

Further, modifying any additives to include additional solid particles and short fibers that improve the overall softness of a substrate is somewhat limited. Many additional particles that can enhance the final hand feel of a substrate require mixing into the dispersion that is sprayed onto the dryer. Because many of these particles are larger than the spray nozzles, clogging of the nozzles is an issue that prevents the additive dispersion from being properly applied onto the dryer surface. Thus, a need exists for a method of applying an additive composition alone or in combination with enhanced softening particles to a dryer surface and eventually a substrate in order to provide a substrate that has improved softness.

SUMMARY OF THE INVENTION

The present invention provides a nonwoven substrate comprising a fibrous web defining a surface; and a layer of a benefit agent wherein said benefit agent is selected from an additive composition, an enhancement component and combinations thereof; wherein said benefit agent is frothed and bonded to the fibrous web surface through a creping process.

The present invention also provides for a method of creping a nonwoven substrate comprising the steps of (a) providing a nonwoven substrate; (b) positioning an applicator adjacent to a hot, non-permeable drying surface; (c) through said applicator, applying to the drying surface an aqueous, frothed, benefit agent; (d) allowing the frothed, benefit agent to form an adhesive film onto the drying surface; (e) directly bonding the nonwoven substrate to the adhesive film positioned on the drying surface; and (f) scraping the bonded nonwoven substrate and adhesive film from the drying surface.

Additionally, the present invention provides for a nonwoven substrate comprising an adhesive film of an aqueous, frothed, benefit agent wherein said benefit agent is selected from an additive composition selected from a synthetic water-soluble polymer, a natural water-soluble polymer and mixtures thereof; an enhancement component selected from the group consisting of micro-particles, thermally expandable microspheres, cut fibers, additional polymer dispersions, fragrances, anti-bacterials, moisturizers, soothers, medicaments and combinations thereof; and mixtures thereof.

BRIEF DESCRIPTION OF THE DRAWINGS

For the purpose of illustrating the invention, there is shown in the drawings a form that is exemplary; it being understood, however, that this invention is not limited to the precise arrangements and instrumentalities shown.

DETAILED DESCRIPTION OF THE INVENTION

Figure 1:
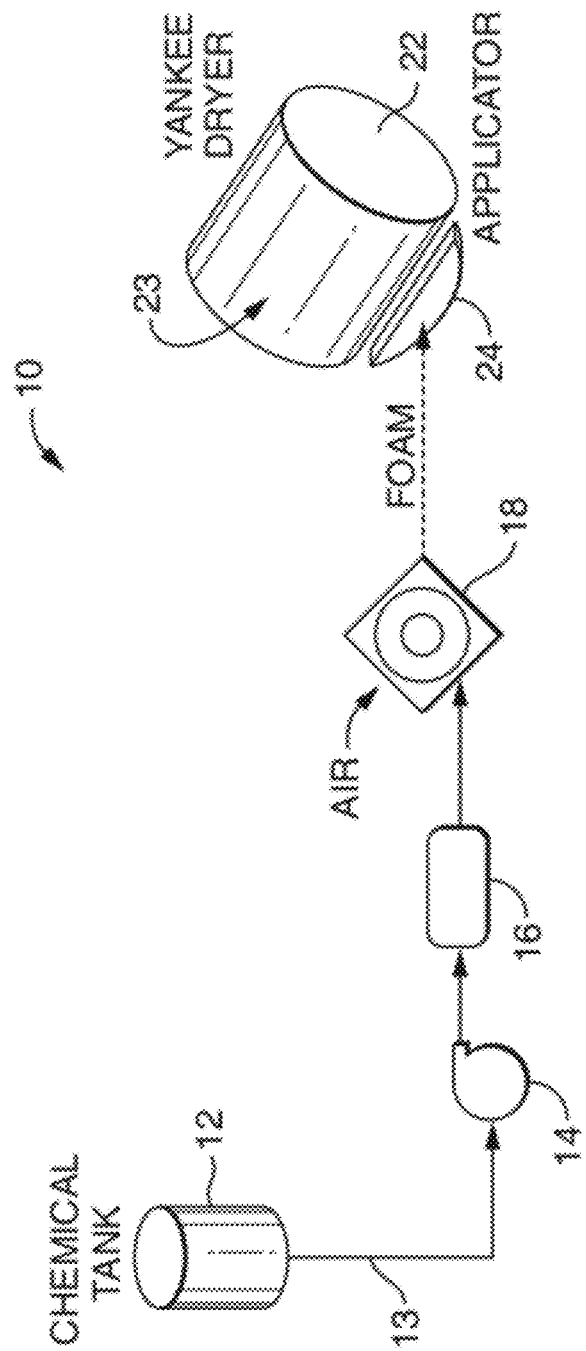
FIG. 1 is a schematic view of process steps used to create one embodiment of a froth according to the present invention.

While the specification concludes with the claims particularly pointing out and distinctly claiming the invention, it is believed that the present invention will be better understood from the following description.

All percentages, parts and ratios are based upon the total weight of the compositions of the present invention, unless otherwise specified. All such weights as they pertain to listed ingredients are based on the active level and, therefore, do not include solvents or by-products that may be included in commercially available materials, unless otherwise specified. The term "weight percent" may be denoted as "wt. %" herein. Except where specific examples of actual measured values are presented, numerical values referred to herein should be considered to be qualified by the word "about".

As used herein, "comprising" means that other steps and other ingredients which do not affect the end result can be added. This term encompasses the terms "consisting of" and "consisting essentially of". The compositions and methods/processes of the present invention can comprise, consist of, and consist essentially of the essential elements and limitations of the invention described herein, as well as any of the additional or optional ingredients, components, steps, or limitations described herein.

"Additive composition" as used herein refers to chemical additives (sometimes referred to as chemical, chemistry, chemical composition and add-on) that are applied topically to a substrate. Topical applications in accordance with the method of the present invention may occur during a drying process, or a converting process. Additive compositions according to the present invention may be applied to any substrate (e.g. tissues or nonwovens) and may include, but are not limited to, polymer dispersions, polymer solutions or mixtures thereof.

"Airlaid web" as used herein is made with an air forming process, wherein bundles of small fibers, having typical lengths ranging from about 3 to about 52 millimeters (mm), are separated and entrained in an air supply and then deposited onto a forming screen, usually with the assistance of a vacuum supply. The randomly deposited fibers are then bonded to one another using, for example, hot air or a spray adhesive. The production of airlaid nonwoven composites is well defined in the literature and documented in the art. Examples include, but are not limited to, the DanWeb process as described in U.S. Pat. No. 4,640,810 to Laursen et al. and assigned to Scan Web of North America Inc.; the Kroyer process as described in U.S. Pat. No. 4,494,278 to Kroyer et al.; and U.S. Pat. No. 5,527,171 to Soerensen assigned to Niro Separation a/s; and the method of U.S. Pat. No. 4,375,448 to Appel et al. assigned to Kimberly-Clark Corporation, or other similar methods.

"Benefit Agents" are compositions or components that provide benefits to the overall treated substrate such as softness, smoothness, moisture, scents, and the like. Benefit agents of the present invention include, but are not limited to "additive compositions" and "enhancement components".

"Bonded Carded Web" or "BCW" refers to a nonwoven web formed by carding processes as are known to those skilled in the art and further described, for example, in U.S. Pat. No. 4,488,928, which is incorporated herein by reference to the extent it is consistent to the present invention. In the carding process, one may use a blend of staple fibers, bonding fibers, and possibly other bonding components, such as an adhesive. These components are formed into a bulky ball that is combed or otherwise treated to create a substantially uniform basis weight. This web is heated or otherwise treated to activate any adhesive component, resulting in an integrated, lofty, nonwoven material.

"Coform" as used herein is a meltblown polymeric material to which fibers or other components may be added. In the most basic sense, coform may be made by having at least one meltblown die head arranged near a chute through which other materials are added to the meltblown materials as the web is formed. These "other materials" may be natural fibers, superabsorbent particles, natural polymer fibers (for example, rayon) and/or synthetic polymer fibers (for example, polypropylene or polyester). The fibers may be of staple length. Coform material may contain cellulosic material in an amount from about 10% by weight to about 80% by weight, such as from about 30% by weight to about 70% by weight. For example, in one embodiment, a coform material may be produced containing pulp fibers in an amount from about 40% by weight to about 60% by weight.

"Creping" as defined herein occurs when a web that is adhered to a dryer surface is scraped off with a blade, such as a doctor blade.

"Enhancement Components" of the present invention are benefit agents that are additional components that may be added to the additive composition in order to impart other tactile or additional benefits that cannot be achieved by the additive composition alone. The enhancement components include, but are not limited to, microparticles, expandable microspheres, fibers, additional polymer dispersions, scents, anti-bacterials, moisturizers, medicaments, soothers, and the like.

"Froth" as defined herein is a liquid foam. According to the present invention, when the frothable composition of the present invention is heated on the dryer's surface, it will not form a solid foam structure. Instead, when applied to a heated surface, the frothable composition turns into a substantially continuous film with air bubbles inside the film.

"Hydroentangled web" according to the present invention refers to a web that has been subjected to columnar jets of a fluid causing the web fibers to entangle. Hydroentangling a web typically increases the strength of the web. In one aspect, pulp fibers can be hydroentangled into a continuous filament material, such as a "spunbond web." The hydroentangled web resulting in a nonwoven composite may contain pulp fibers in an amount from about 50% to about 80% by weight, such as in an amount of about 70% by weight. Hydroentangled composite webs as described above are commercially available from the Kimberly-Clark Corporation under the name HYDROKNIT®. Hydraulic entangling is described in, for example, U.S. Pat. No. 5,389,202 to Everhart.

"Nonwoven" is defined herein as a class of fabrics generally produced by attaching fibers together. Nonwoven fabric is made by mechanical, chemical, thermal, adhesive, or solvent means, or any combination of these. Nonwoven manufacture is distinct from weaving, knitting, or tufting. Nonwoven fabrics may be made from synthetic thermoplastic polymers or natural polymers such as cellulose. Cellulosic tissue is one example of a nonwoven material.

"Meltblowing" as used herein is a nonwoven web forming process that extrudes and draws molten polymer resins with heated, high velocity air to form fine filaments. The filaments are cooled and collected as a web onto a moving screen. The process is similar to the spunbond process but meltblown fibers are much finer and generally measured in microns.

"Processing Aids" as used herein refer to compositions that may help in the process of forming the treated substrate of the present invention. For example, foaming agents may serve as suitable processing aids of the present invention. Additionally, creping aids may help with additional adhesion or release properties for creping the substrate from a dryer drum.

"Spunbond" as used herein is a nonwoven web process in which the filaments have been extruded, drawn and laid on a moving screen to form a web. The term "spunbond" is often interchanged with "spunlaid," but the industry has conventionally adopted the spunbond or spunbonded terms to denote a specific web forming process. This is to differentiate this web forming process from the other two forms of the spunlaid web forming, which are meltblowing and flashspinning.

"Spunbond/Meltblown composite" as used herein is a laminar composite defined by a multiple-layer fabric that is generally made of various alternating layers of spunbond ("S") webs and meltblown ("M") webs: SMS, SMMS, SSMMS, etc.

"Tissue" as used herein generally refers to various paper products, such as facial tissue, bath tissue, paper towels, table napkins, sanitary napkins, and the like. A tissue product of the present invention can generally be produced from a cellulosic web having one or multiple layers. For example, in one embodiment, the cellulosic or "paper" product can contain a single-layered paper web formed from a blend of fibers. In another embodiment, the paper product can contain a multi-layered paper (i.e., stratified) web. Furthermore, the paper product can also be a single- or multi-ply product (e.g., more than one paper web), wherein one or more of the plies may contain a paper web formed according to the present invention.

The present invention is an alternative to the current method of spraying onto a dryer surface (e.g. the drum of a Yankee dryer or a hot calender) an aqueous dispersion or a solution of creping chemicals. In contrast to liquid chemistry, the frothed chemistry has enough structural integrity to reach the dryer surface against gravity due to significant high viscosity. By creating a frothed chemistry according to the present invention, a chemistry applicator can be placed in much closer proximity to the dryer surface. Additionally, by utilizing the frothed chemistry of the present invention, it is feasible to incorporate additional benefits that were otherwise more difficult to apply.

Another advantage of the present invention is that less energy is consumed by the dryer. The close proximity of the chemistry applicator to the dryer surface improves chemical mass efficiency (i.e., decrease waste in application process) and energy efficiency. Efficiency is increased because the air introduced into the froth of the present invention acts as a diluter. As a result, less heat is required to remove water from the frothed creping chemistry (i.e., benefit agents) during the drying process. This is an improvement over the spraying process which uses water to dilute the benefit agent.

Further, after the creping step, a layer of the benefit agent remains on the nonwoven substrate surface in order to add more bulk and softness. This increase in bulk is due to the entrapped air inside the coated layer. The enhanced softness is due to the benefit agents that can be frothed onto the dryer surface and subsequently transferred or adhered to the surface of the substrate through the creping process. Though the frothed benefit agents become a film during the drying step, not all of the air entrapped in the froth is lost during the drying step due to the higher viscosity associated with higher solid-levels in the frothed additive composition.

Various substrates other than tissue may be treated in accordance with the present disclosure. Examples include, but are not limited to, wet-laid webs, airlaid webs, spunbond webs, coform webs, bonded & carded webs (BCW), continuous film, and hydroentangled webs. The benefit agent is typically applied on one side of any substrate, but could be applied to both sides as desired.

Benefit Agents
I. Additive Composition

In a desired application, the additive composition may be present at a level from about 50 $mg/m^2$ to about 10,000 m $g/m^2$, or from about 50 $mg/m^2$ to about 1000 $mg/m^2$ or from about 100 $mg/m^2$ to about 1000 $mg/m^2$. The difference between these suggested ranges is dependent on whether or not the additive composition is applied to a substrate either in-line (such as a tissue machine), or an off-line machine (such as a non-woven converting line). Additive compositions of the present invention may be in the form of a polymer dispersion or a polymer solution as set forth below.

A. Polymer Dispersions

Frothable compositions of water insoluble polymers may be in the form of dispersions. The water insoluble polymer materials that are solids, such as powder, granules, and the like, may be converted into a frothable dispersion by mixing it with water and surfactant(s) under certain processing conditions such as high pressure extrusion at an elevated temperature. The polymer dispersion may then be mixed with air and a foaming agent to convert it into a froth.

Examples of dispersions according to the present invention include, but are not limited to, a polyolefin dispersion such as HYPOD 8510®, commercially available from Dow Chemical, Freeport, Tex., U.S.A.; polyisoprene dispersion, such as KRATON®, commercially available from Kraton Polymers U.S. LLC, Houston, Tex., U.S.A.; polybutadiene-styrene block copolymer dispersion such as Butanol®, commercially available from BASF Corporation, Florham Park, N.J., USA; latex dispersion such as E-PLUS®, commercially available from Wacker, Munich, Germany; polyvinyl pyrrolidone-styrene copolymer dispersion and polyvinyl alcohol-ethylene copolymer dispersion, both are available from Aldrich, Milwaukee, Wis., U.S.A.

B. Polymer Solutions

Frothable compositions of water soluble polymers may also be in the form of solutions. The water-soluble polymer materials that are solids, such as powder, granules, and the like, may be dissolved into a solution. The polymer solution may then be mixed with air and a foaming agent to convert it into a froth.

Examples of polymer solutions according to the present invention include both synthetic and natural based water soluble polymers. The synthetic water soluble polymers include, but are not limited to, polyalcohols, polyamines, polyimines, polyamides, polycarboxlic acids, polyoxides, polyglycols, polyethers, polyesters, copolymers and mixtures of the listed above.

The natural based water soluble polymers include, but are not limited to, modified cellulose, such as cellulose ethers and esters, modified starch, chitosan and its salts, carrageenan, agar, gellan gum, guar gum, other modified polysaccharides and proteins, and combinations thereof. In one particular embodiment, the water soluble polymers also include: poly (acrylic acid) and salts thereof, poly(acrylate esters), and poly(acrylic acid) copolymers. Other suitable water soluble polymers include polysaccharides of sufficient chain length to form films such as, but not limited to, pullulan and pectin. For example, the water soluble polymers may contain additional monoethylenically unsaturated monomers that do not bear a pendant acid group, but are copolymerizable with monomers bearing acid groups. Such compounds include, for example, the monoacrylic esters and monomethacrylic esters of polyethylene glycol or polypropylene glycol, the molar masses (Mn) of the polyalkylene glycols being up to about 2,000, for example.

In another particular embodiment, the water soluble polymers may be hydroxypropyl cellulose (HPC) sold by Ashland, Inc. under the brand name of KLUCEL®. The water soluble polymers can be present in the additive composition in any operative amount and will vary based on the chemical component selected as well as on the end properties that are desired. For example, in the exemplary case of KLUCEL®, the biodegradable, water soluble polymers can be present in the additive composition in an amount of about 1% to about 75%, or at least about 1%, at least about 5%, or at least about 10%, or up to about 30%, up to about 50% or up to about 75%, based on the total weight of the additive composition, to provide improved benefits. Other examples of suitable water soluble polymers include methyl cellulose (MC) sold by Ashland, Inc. under the brand name BENECEL®; hydroxyethyl cellulose sold by Ashland, Inc. under the brand name NATROSOL®; and hydroxypropyl starch sold by Chemstar (Minneapolis, Minn., U.S.A.) under the brand name GLUCOSOL 800®. Any of these chemistries, once diluted in water, are disposed onto a hot, non-porous dryer surface to ultimately transfer the chemistry to the web surface. The water soluble polymers in these chemistries include, but are not limited to, polyvinyl alcohol, polyethylene glycol, polyethylene oxide, hydroxypropyl starch, hydroxypropyl cellulose, and combinations thereof.

Conventional creping chemistries for tissue manufacturing may include water-soluble polymer solutions, such as an aqueous mixture comprising polyvinyl alcohol and a polyamide-epihalohydrin resin. While these conventional creping chemistries comprise water-soluble polymer solutions, these are not able to provide the benefits of the present invention, which include enhanced softness without compromising the strength of the tissue sheet.

The additive composition of the present invention may be commercially available, such as HYPOD 8510® dispersion, from the Dow Chemical Corporation and consists of water, a polyethylene-octene copolymer, and a copolymer of ethylene and acrylic acid. The polyethylene-octene copolymer may be obtained commercially from the Dow Chemical Corporation under the name AFFINITY® (type 29801) and the copolymer of ethylene and acrylic acid may be obtained commercially from the Dow Chemical Corporation under the name PRIMACOR® (type 59081). PRIMACOR® acts as a surfactant to emulsify and stabilize AFFINITY® dispersion particles. The acrylic acid co-monomer of PRIMACOR® is neutralized by potassium hydroxide to a degree of neutralization of around 80%. Therefore, in comparison, PRIMACOR® is more hydrophilic than is AFFINITY®. In a dispersion, PRIMACOR® acts as a surfactant or a dispersant. Unlike PRIMACOR®, AFFINITY®, as suspended in a dispersion, takes on a form of tiny droplets with a diameter of a few microns. PRIMACOR® molecules surround the AFFINITY® droplets to form a "micelle" structure that stabilizes the droplets. HYPOD 8510® contains about 60% AFFINITY® and 40% PRIMACOR®.

When the dispersion becomes a molten liquid on the dryer's hot surface, AFFINITY® forms a continuous phase and PRIMACOR® a dispersing phase forming islands in the AFFINITY® "ocean." This phase change is called phase inversion. However, occurrence of this phase inversion depends upon external conditions such as temperature, time, molecular weight of solids, and concentration. Ultimately, phase inversion only occurs when the two polymers (or two phases) have enough relaxation time to allow phase inversion completion. In the present invention, HYPOD 8510® coated film retains a dispersion morphology which indicates there is an incompletion of phase inversion. Benefits of the remaining dispersion morphology include, but are not limited to, a more hydrophilic coating layer due to the exposure of the PRIMACOR® phase; and more improved softness of the coated product due to entrapped air bubbles inside the coated HYPOD 8510® layer which provide extra bulkiness.

The diluted dispersion may have a very low viscosity (around 1 cp, just like water). A low viscosity dispersion, when applied onto a hot dryer drum, will undergo a process of water evaporation and a complete phase inversion of AFFINITY®. The resulting continuous molten film then has PRIMACOR® dispersion islands embedded therein. The film formed after completely evaporating the water is solid without any air bubbles entrapped therein. After transferring the molten film onto a the web through the creping process, the thin film covering the surface of the treated tissue is discontinuous yet interconnected, see FIG. 6c, discussed infra.

The process of the present invention may use a high solid, high viscosity dispersion of (about 10% to about 30%) and may contain a large amount of air bubbles (air volume is at least 10 times more than the dispersion volume). Desirably, the commercially available HYPOD 8510® dispersion (about 42% solids, including both AFFINITY® and PRIMACOR®) has a viscosity around about 500 cps whereas water has a viscosity of around about 1 cps. A dispersion containing about 20% HYPOD 8510® may have a viscosity of around 200 cps, a relatively high viscosity, while a dispersion having less than about 1% HYPOD 8510® may have a viscosity closer to water's viscosity (1 cp). After entrapping a high ratio of air, the viscosity of the frothed HYPOD 8510® dispersion has been increased exponentially compared to the dispersion before being frothed.

Referring to FIG. 1, when a frothed dispersion is applied onto the non-porous dryer surface 23, a limited amount of water will be quickly evaporated therefrom. It is thought that the dispersion's slow evaporation due to high solids combined with its high viscosity will prevent the AFFINITY®-PRIMACOR® dispersion from completing a phase inversion (wherein the AFFINITY® becomes continuous and the PRIMACOR® becomes a dispersion) and entrapped air from escaping. This results in a unique micro-structured molten film on the hot dryer surface.

Figure 6:
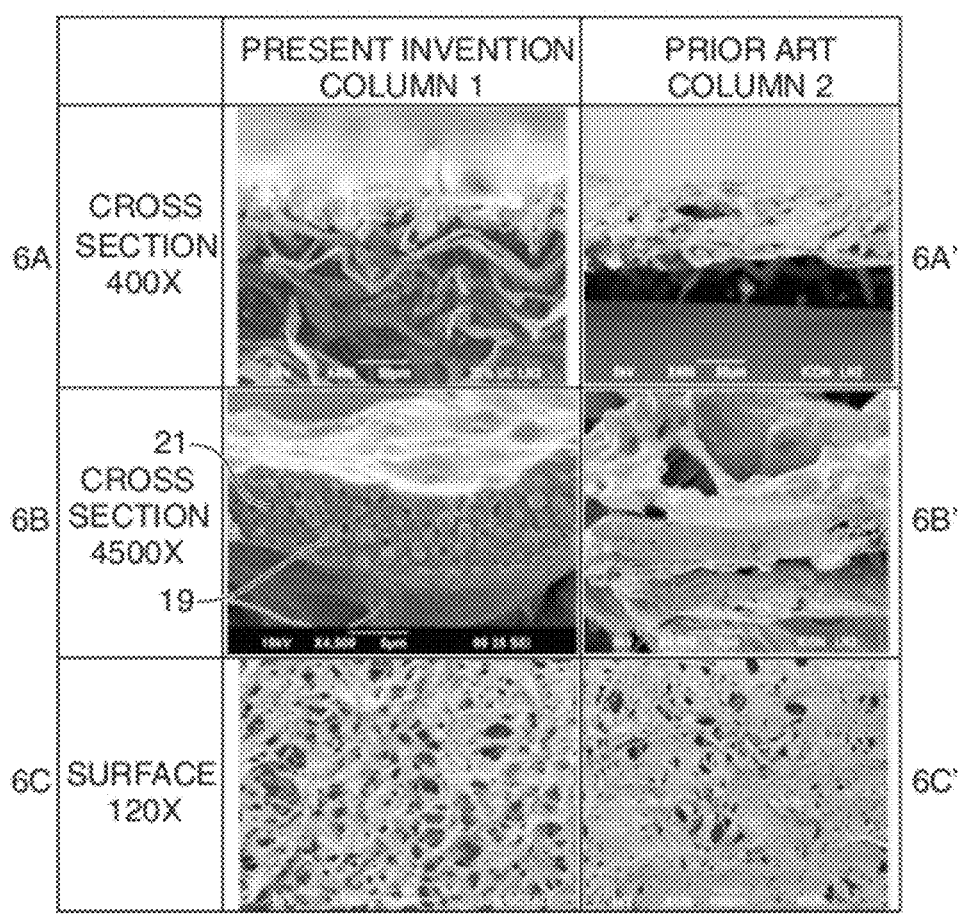
FIG. 6 is a series of SEM photographs showing the structural change of a tissue material after being treated by one embodiment of a method of the present invention.

Referring to FIG. 6, the SEM photos confirm the foregoing hypothesis. Two immediate benefits can be observed when comparing the prior art surface-treated tissues and the surface-treated tissues of the present invention. First, the method of the present invention yields a tissue that is more bulky and has a softer hand feel due to entrapment of air bubbles 21 (see FIG. 6b). Second, the tissue of the present invention has a more wettable surface due to incomplete phase inversion, which in turn results in surface exposure of the hydrophilic component.

Visually compare FIGS. 6a, 6b, 6c to FIGS. 6a', 6b', 6c'. The coated layer having dispersion beads 19 and entrapped air bubbles 21 shown in FIG. 6b, is softer than the melted film shown in FIG. 6b' as determined by the In Hand Ranking Test disclosed herein.

II. Enhancement Components

The present invention not only provides a substrate with improved softness due to the benefit agents and process described herein, but it also provides for an improved hand feel. Enhancement components are added to the dispersions of the present invention to provide a cottony/fluffy feel to the substrate instead of the silky/slippery feel that may often be felt with the use of the dispersions alone. While the silky/slippery feel may be desirable for some substrates, the present invention provides other options in order that a variety of textures and aesthetics can be provided. Enhancement components of the present invention include, but are not limited to, micro-particles such as silica gel particles, thermally expandable microspheres such as EXPANCEL®, fibers such as cotton linter flocks, polymer dispersions such as poly(vinylpyrrolidone-styrene), and combinations thereof. When cotton linter flocks or other types of fibers are used, they may be from about 0.1 mm fiber length to about 5 mm fiber length.

In addition to the enhancement components providing a contrasting hand feel, the enhancement components may also provide additional benefits that could not be appreciated with the use of the dispersion alone. Enhancement components of the present invention may also include fragrances, anti-bacterials, moisturizers, soothers, medicaments and combinations thereof. Such components will provide an overall substrate that has improved feel from the dispersion in combination with benefits that may have not otherwise been provided without the present technology. The present invention may utilize any or a combination of enhancement components to be included within the additive composition of the present invention. For example, enhancement components may be added to a dispersion of the present invention in an amount of from about 0.5% to about 30%, from about 1% to about 20% or from about 2% to about 10%, by weight of the dispersion composition.

The enhancement components can be added into the frothed chemistry either before or after the chemistry has been frothed. In a desired application, the enhancement component level is about from about 0.5% to about 30%, or from about 1% to about 20%, or from about 2% to about 10%, based on total dry weight of the additive composition.

Figure 14:
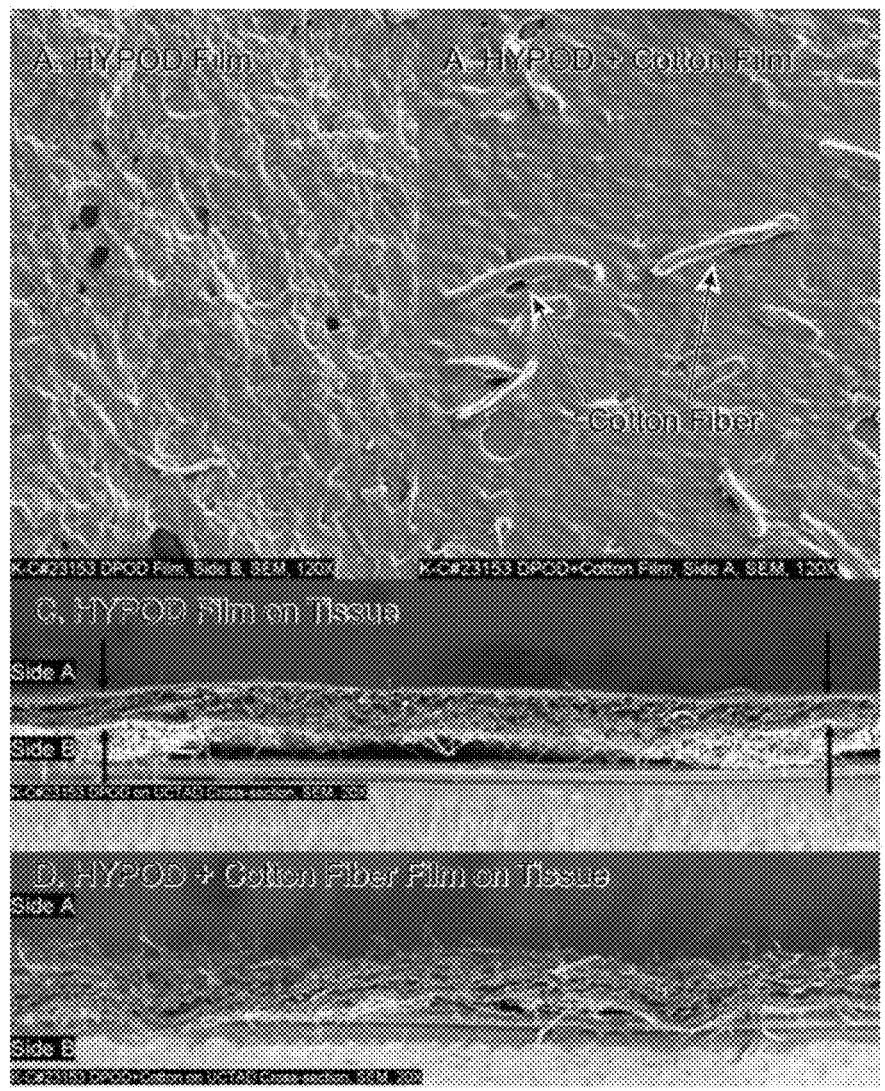
FIG. 14 illustrates both surface and cross-sectional morphological structures of a surface coated with an enhancement component of the present invention.

When enhancement components are used in combination with the additive compositions of the present invention, they allow for enhanced softness without compromising strength. For example, when facial tissue is used as the substrate of the present invention, there is an overall log odds increase of from about 0.5 to about 18 and a GMT level of from about 800 to about 1200 when compared to substrates that have not been processed in the same manner as the present invention. "GMT" as used herein refers to the combination of machine and cross-machine directions in determining tensile strength. As shown in FIG. 14, both surface and cross-sectional morphological structures are represented in photos A and B. Enhancement component cotton linter flock fibers are clearly shown on the surface. In Photos C and D, the cotton linter flock fiber makes the creped tissue surface much more "cottony" or "fluffy" than that of HYPOD 8510® alone as the benefit agent.

Figure 15:
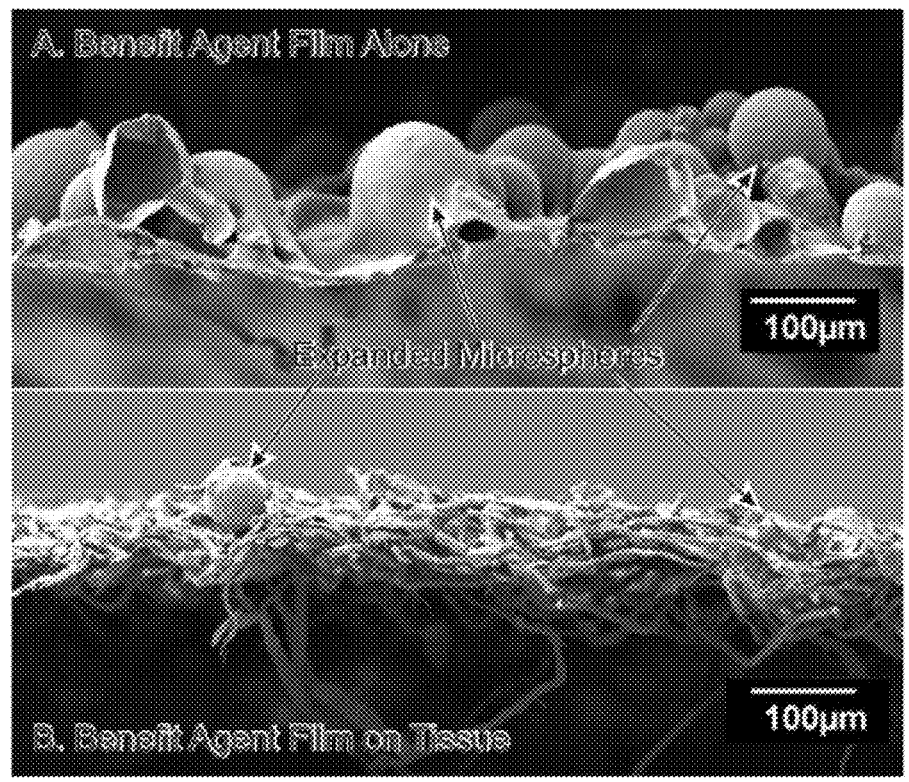
FIG. 15 shows both a coated film and a tissue comprising a combination benefit agent of the present invention.

FIG. 15 shows both the coated film and the tissue of a combination benefit agent wherein HYPOD 8510® is the additive composition and Expancel® expandable microspheres is the enhancement component. It is clearly shown that expanded microspheres stay on the surface of both film and tissue which will contribute to hand feel improvement when consumers touch them in use conditions.

III. Processing Aids

Processing aids of the present invention include chemicals that may help in the process of forming the treated substrate of the present invention. The processing aids may slightly appear or may dissipate in the final, treated substrate. While they are included to solely aid in the process of producing the treated substrates, they may also impart slight benefits to the substrate that are desired of the present invention. For the purposes of this application, "processing aids" are those used in the process of frothing or applying the benefit agents to the substrate and are not used in the process of making the precursor substrate.

A. Foaming Agents

Most commercial foaming agents are suitable for creating the froth of the present invention. Suitable foaming agents include, but are not limited to, either low molecular or polymeric materials in liquid form. The foaming agents can be anionic, cationic or nonionic. These foaming agents can be divided into four groups depending on function:

1. Air Entrapment Agent—used to enhance a liquid's (dispersion, solution, or a mixture, etc.) capability to entrap air which can be measured by determining a "blow ratio." An exemplary list of foaming agents include but is not limited to potassium laurate, sodium lauryl sulfate, ammonium lauryl sulfate, ammonium stearate, potassium oleate, disodium octadecyl sulfosuccinimate, hydroxypropyl cellulose, etc.
2. Stabilization Agent—used to enhance stability of froth's air bubbles against time and temperature; examples include, but are not limited to, sodium lauryl sulfate, ammonium stearate, hydroxypropyl cellulose, etc.
3. Wetting Agent—used to enhance the wettability of a film-coated dried surface. Examples include, but are not limited to, sodium lauryl sulfate, potassium laurate, disodium octadecyl sulfosuccinimate, etc.
4. Gelling Agent—used to stabilize air bubbles in the froth by causing the additive composition to take the form of a gel which serves to reinforce cell walls. Examples include, but are not limited to, hydroxypropyl cellulose, hydroxyethyl cellulose, carboxymethyl cellulose and other modified cellulose ethers.

Some foaming agents can deliver more than one of the functions listed above. Therefore, it is not necessary to use all four foaming agents in a frothable additive composition. Selection of the foaming agents is dependent upon the chemistry of the additive composition. For example, when the additive composition comprises an anionic component, such as HYPOD 8510®, suitable foaming agents have to be selected from either anionic or non-ionic groups. If a cationic foaming agent is used to enhance frothability of an anionic additive composition, the cationic components in the foaming agent will form ionic bonds with the anionic components in the additive composition and cause both cationic foaming agent and anionic additive composition to become water insoluble due to formation of the bonds. On the other hand, if an additive composition comprises cationic components, anionic foaming agents are not suitable to use.

B. Creping Aids

Creping Aids are chemistries that are added to the benefit agents of the present invention to optimize the adhesion and release properties of the tissue substrate to the dryer surface. These fall broadly into the following groupings:

1. Adhesion Aid—used to increase adhesion of the tissue sheet to the dryer surface. Examples include, but are not limited to, polyvinyl alcohol, polyacrylate, hydroxypropy starch, carboxymethy cellulose, kymene, polyvinyl amine, copolymers or mixtures thereof.
2. Release Aid—used to decrease adhesion (enhance release) of the tissue sheet to (from) the dryer surface. Examples include, but are not limited to, polyethylene glycol, polypropylene glycol, polyethylene oxide, polypropylene oxide, polyolefin, fluorinated polyolefin, copolymer and blends comprising the above.

3. Curing Aid—used to hasten or retard curing of the creping package such as a plasticizer or toughener Froth Generating Process In general, preparing frothed chemicals utilizes a system that pumps both liquid and air into a mixer. The mixer blends the air into the liquid to produce a froth which inherently includes a plurality of small air bubbles. The froth exits the mixer and flows to an applicator.

One parameter to define the quality of frothed chemistry is the blow ratio, which is defined by ratio of volume of small air bubbles entrapped by dispersion chemical to the volume of the dispersion before mixing. For example, at a blow ratio of 10:1, a dispersion flow rate of 1 liter/minute will be able to entrap 10 liters/minute of air into its liquid and produce a total froth flow rate of 11 liters per minute.

To achieve a high blow ratio, both the mechanical mixing and the frothing capability of the additive composition are determining factors. If a chemical can only hold or entrap air volume up to a blow ratio of 5, no matter how powerful a froth unit is, it won't be able to produce a stable froth having a blow ratio of 10. Any extra air beyond the blow ratio of 5 will release out of the froth system once the mechanical force is removed. In other words, any entrapped air higher than the dispersion's air containment capability will become instable. Most of such instable air bubbles will escape from the froth (debubbling) immediately after mechanical agitation is stopped.

Referring to FIG. 1, shown schematically, is a system 10 that can generate the frothed chemistry according to the present invention. To begin, frothable chemicals (e.g. HYPOD 8510®, KRATON®, and the like) are placed in a chemical tank 12. The chemical tank 12 is connected to a pump 14. It may be desirable to modify piping 13 between the chemical tank 12 and pump 14 so that one may transmit the frothable chemicals to two different sizes of pumps. Desirably the chemical tank 12 is situated at an elevated level above the pump 14 in order to keep the pump primed.

One optional small secondary pump (not shown) may be used for running the frothing process at slow speeds relative to the pump 14. The larger primary pump 14 is capable of producing flow rates up to 25 liters/minute liquid flow-rate for high application speeds and/or high amounts of additive composition. The smaller, secondary pump (not shown) is capable of liquid flow rates up to about 500 cc/min. for low application speeds and/or low additive composition.

A flow meter 16 is situated between the pump(s) 14 and a foam mixer 18. Liquid flow rates are calculated from desired additive composition, chemical solids, line-speed and applicator width. The flow rate may range from about 5:1 to about 50:1. When using the small secondary pump, its flow rate ranges from about 10 cc/min to about 500 cc/min. When using the large pump 14, its flow rate ranges from about 0.5 liter/min to about 25 liter/min. A 20 liter/min air flow meter is selected when using the small secondary pump. There is a 200 liter/min air flow meter to use when running the larger primary pump 14.

In one aspect, the foam mixer 18 is used to blend air into the liquid mixture of frothable chemicals to create small air bubbles in the froth. Air is metered into the system 10 using certain liquid flow rates and blow ratios as discussed above. Desirably, the foam mixer 18 having a size of 25.4 cm (10 inches) may be used to generate froth. One possible foam mixer 18 is a CFS-10 inch Foam Generator from Gaston Systems, Inc. of Stanley, N.C., U.S.A.

Desirably, the rotational speed of the foam mixer 18 is limited to about 600 rpm. The rpm speed for the mixer in this process is dependent upon the additive composition's ability to foam (i.e., its capability of entrapping air to form stable bubbles). If the additive composition foams easily, a lower rpm is generally required. If the additive composition does not foam easily, a higher rpm is generally required. The higher mixer speed helps to speed up the foam equilibrium or optimal blow ratio. A normal rpm for the mixer is about 20%-60% of the maximum rpm speed. The type of and/or amount of foam agent in addition to the additive composition also has an effect on the mixer speed requirement.

The froth is checked for bubble uniformity, stability and flow pattern. If bubble uniformity, stability and flow pattern are not to desired standards, adjustments may be made to flow rates, mixing speeds, blow ratio, and/or chemical compositions of the solutions/dispersions before directing the froth to the applicator 24.

In one aspect of the invention, HYPOD 8510®, or other chemistries to be frothed and used for creping are blended and added to the chemical tank 12. Dilute solutions of HYPOD 8510 (<10% total solids) and other hard-to-froth chemistries generally require something added to the formulation to increase viscosity and foamability. For example, hydroxypropyl cellulose or other foaming agents or surfactants, can be used to produce a stable froth for uniform application onto the heated and non-permeable surface of a rotating drum of a dryer surface. The enhancement components, such as silica gel particles or cotton linter flocks, can be added into the additive composition in various ways, including, but not limited to: added into the additive composition before the additive composition is pumped into a frothing machine; introduced into the frothed additive composition after the additive composition is coming out of the frothing machine but before the frothed additive composition is applied onto the dryer's surface; or applied to the dryer before the substrate contacts the additive composition. When the enhancement components are introduced into the additive composition, it is necessary to constantly agitate the mixture before adding it into the frothing machine in order to prevent the solid enhancement component from being settled down at the bottom of the container. When the enhancement components are introduced into the frothed additive composition, a suitable device, which ensures a uniform mixing of the enhancement components and the frothed additive composition, is needed.

Substrates

Suitable substrate materials include but are not limited to facial tissue; uncreped through air-dried tissue (UCTAD); paper toweling; HYDROKNIT® nonwoven material from Kimberly Clark Corporation, Neenah, Wis., U.S.A.; spunbond; coform; bonded carded web ("BCW"); airlaid, film/laminate sheet, and all types of paper, tissue and other nonwoven products.

Figure 4:
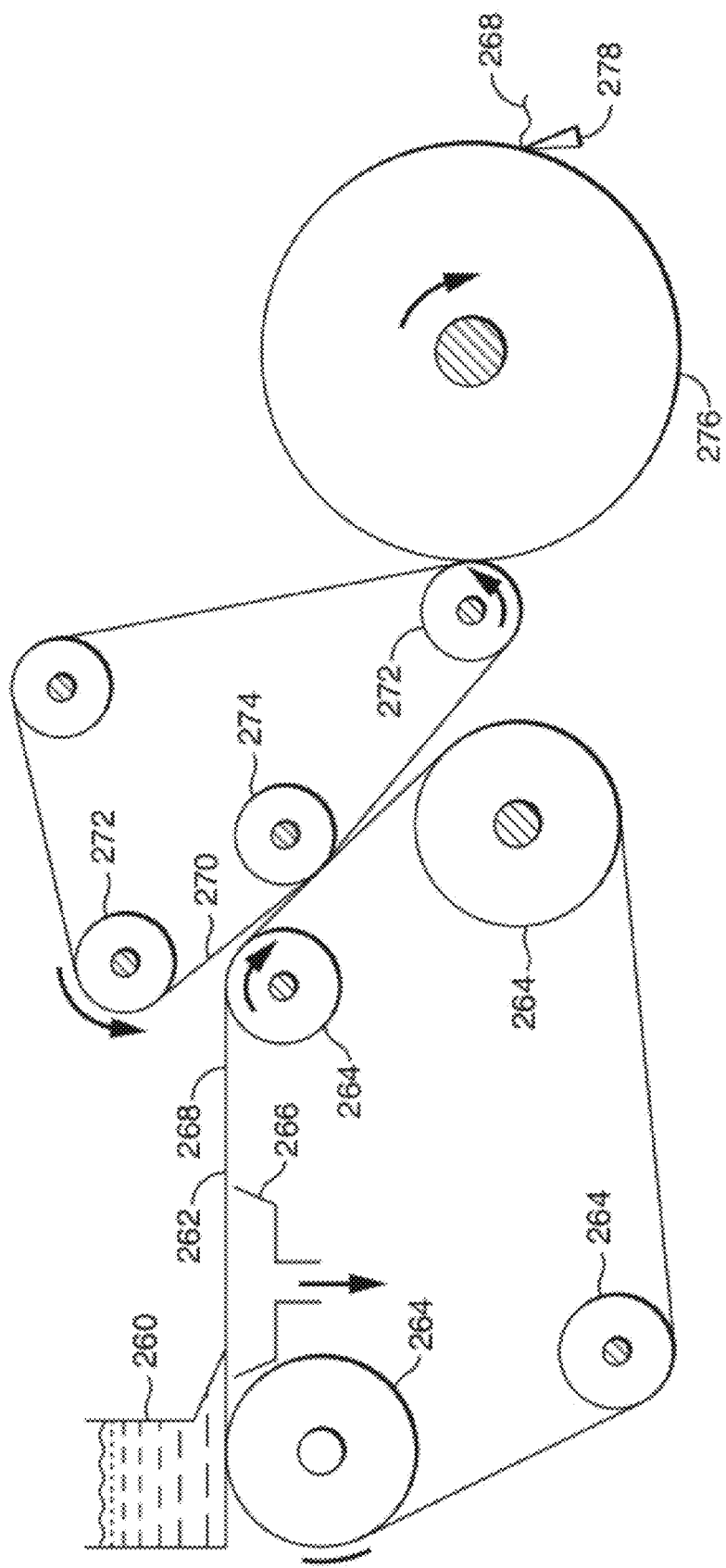
FIG. 4 is a schematic view of a tissue manufacturing process using creping equipment.
Figure 5:
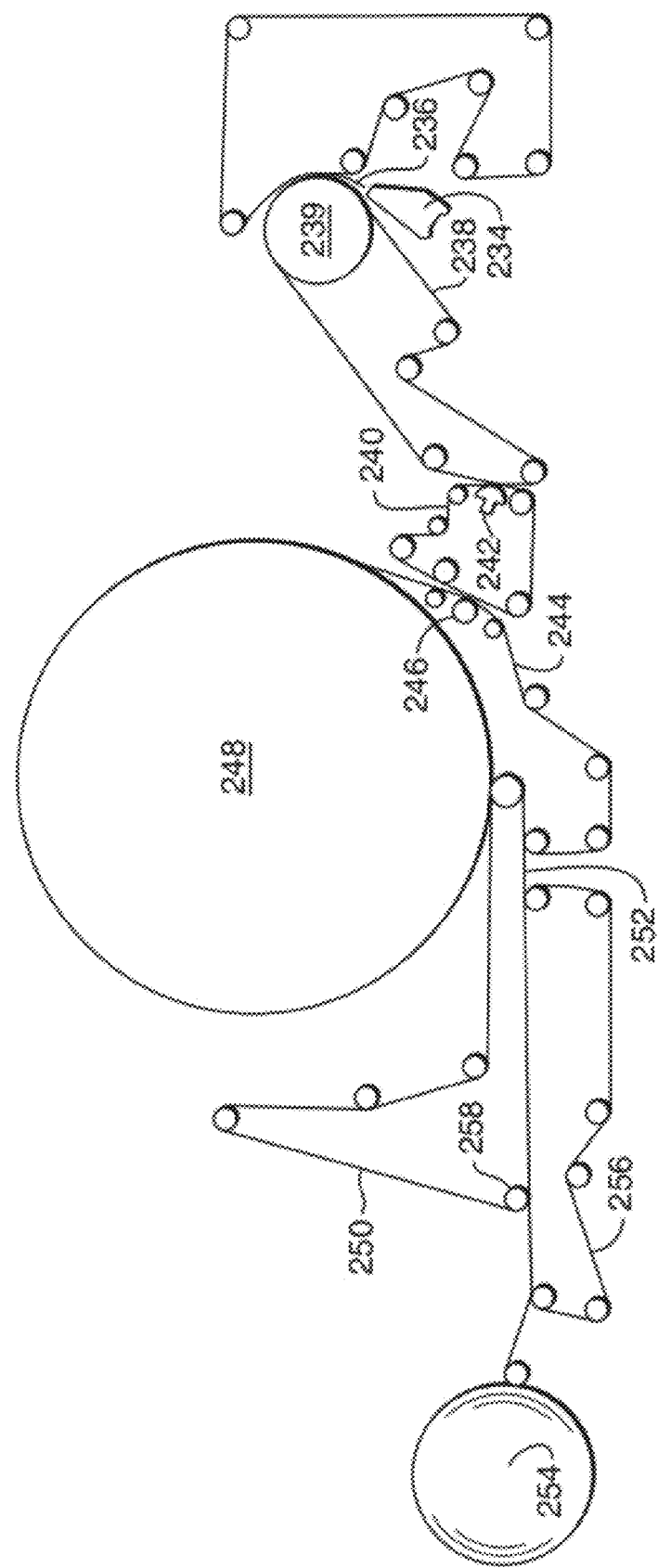
FIG. 5 is a schematic view of a tissue manufacturing process that does not include creping equipment.

In the non-limiting examples discussed herein, the frothed chemistry may be applied to a nonwoven such as a tissue. As used herein, nonwovens are meant to include facial tissue, bath tissue, paper towels, spunbond, diaper or feminine care liners and outer covers, napkins and the like. Tissue may be made in different ways, including but not limited to conventionally felt-pressed tissue paper; high bulk pattern densified tissue paper; and high bulk, uncompacted tissue paper. Tissue paper products made therefrom can be of a single-ply or multi-ply construction such as in US Patent Publication No. 2008/0135195. Shown in FIG. 4 is one embodiment of a process for forming a wet creped tissue web of the present invention. The additive composition may be applied to the surface of the dryer drum 276 for transfer onto one side of the tissue web 268. In this manner, the additive composition adheres the tissue web 268 to the dryer drum 276. In this embodiment, as web 268 is carried through a portion of the rotational path of the dryer surface, heat is imparted to the web causing most of the moisture contained within the web to be evaporated. Web 268 is then removed from the dryer drum 276 by a creping blade 278. Creping the web 268 as it is formed further reduces internal bonding within the web and increases softness.

Another embodiment for forming a tissue of the present invention utilizes a papermaking technique known as uncreped through-air dried ("UCTAD"). Examples of such a technique are disclosed in U.S. Pat. No. 5,048,589 to Cook, et al.; U.S. Pat. No. 5,399,412 to Sudall, et al.; U.S. Pat. No. 5,510,001 to Hermans, et al.; U.S. Pat. No. 5,591,309 to Rugowski, et al.; and U.S. Pat. No. 6,017,417 to Wendt, et al.

Surface Coating Process

Unlike a process that sprays a dilute dispersion or solution onto a dryer surface such as a Yankee dryer surface 23 (or other suitable dryer drum surface (not shown)), the process of the present invention can apply high-solid frothed chemistry onto the dryer surface 23. In the present invention, air is used to dilute a benefit agent comprising any level of solids wherein the viscosity is within a range that can be pumped by the foaming machine. For example, having up to about 65% of solids, up to about 50% solids, up to about 35%, or up to about 20% solids.

The high-solid coating process of the present invention may exhibit product or process benefits including but not limited to softer surface due to the unique micro-structure of the coated layer (see, FIG. 6); less chemical waste due to close and direct application of the frothed chemistry; and no need to use soft or deionized water due to the high ratio of chemistry to water (for example, a chemical such as HYPOD 8510® becomes instable when it is exposed to a large quantity of hard water, i.e., a solid level of 1% or less); and less drying energy required to dry the frothed chemistry as well as the base sheet. Additional benefits due to the addition of enhancement components include, but are not limited to uniformity of the overall Benefit Agent film coating on the nonwoven substrate; enhanced adhesion of the overall Benefit Agent coating to the nonwoven substrate; enhance mechanical strength of the overall Benefit Agent coating film; and enhanced stability of the Benefit Agent froth from the foam generator unit to the dryer surface.

The frothed benefit agents may be applied onto a substrate 27 by two ways: an inline application or an offline application. In the inline processes a foam generator and an applicator depicted in FIGS. 1 and 2, will be incorporated into a tissue manufacturing line as shown in FIG. 4 and the frothed chemicals will be applied onto any substrate 27 during the manufacture of same. Referring to FIG. 3, the offline application enables application of the froth chemistry to those substrates 80 which are produced by a non-creping process. For example, uncreped through air dried ("UCTAD") bath tissue and melt-spun nonwoven materials are suitable for use with the offline application method.

Referring to FIG. 1, in one aspect of the invention, the frothed chemicals are applied to the dryer surface 23 via an applicator 24. The froth applicator 24 is placed close to the dryer surface (0.64 cm or ¼ inch) for uniform froth distribution onto the dryer surface 23. Such positioning allows for better, direct contact of the frothed chemistry to the dryer surface 23, especially during high speed operations.

Figure 2:
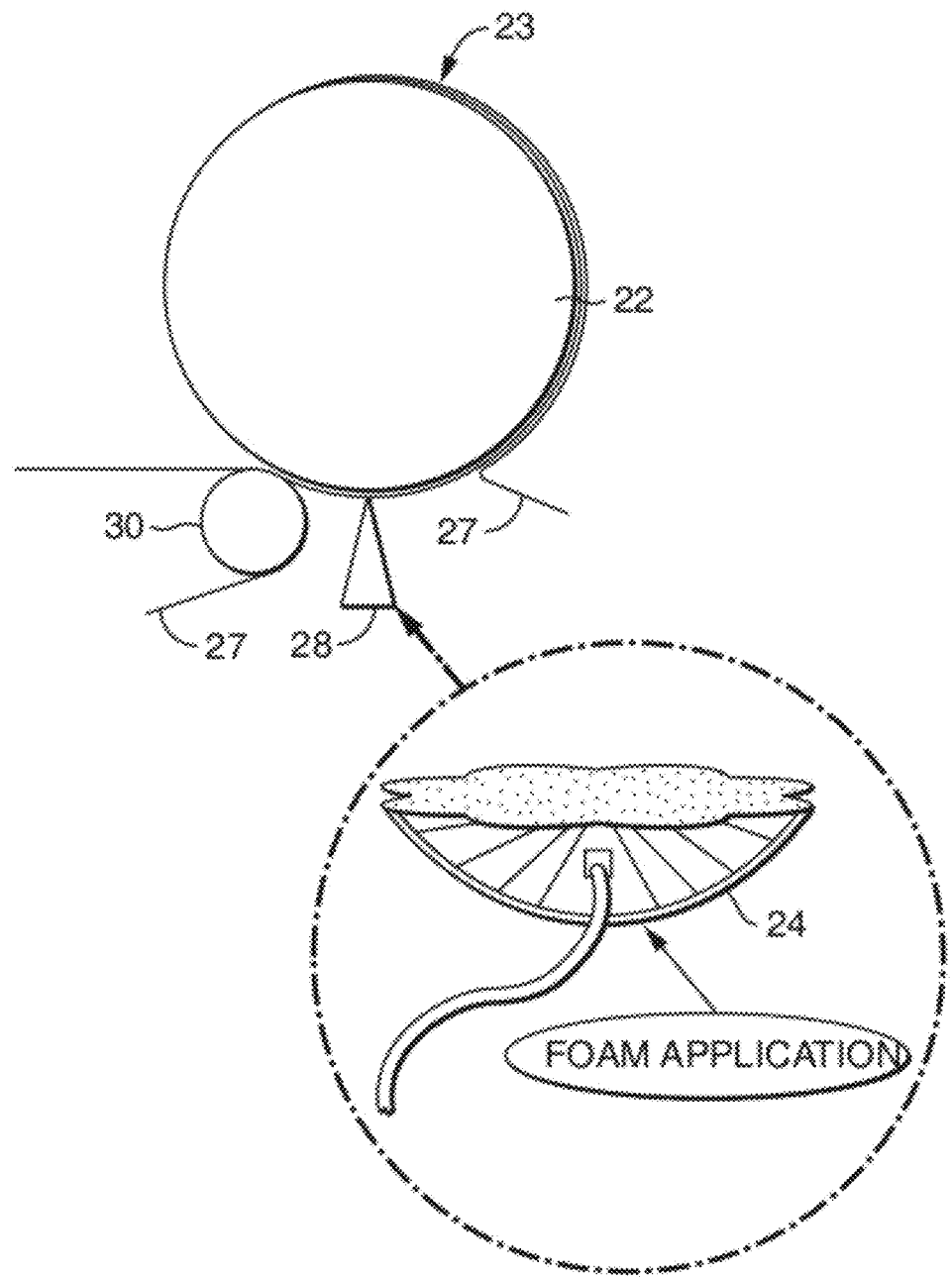
FIG. 2 is a side schematic view of the Yankee dryer of FIG. 1, showing the froth application to the dryer surface according to one embodiment of the present invention.
Figure 3:
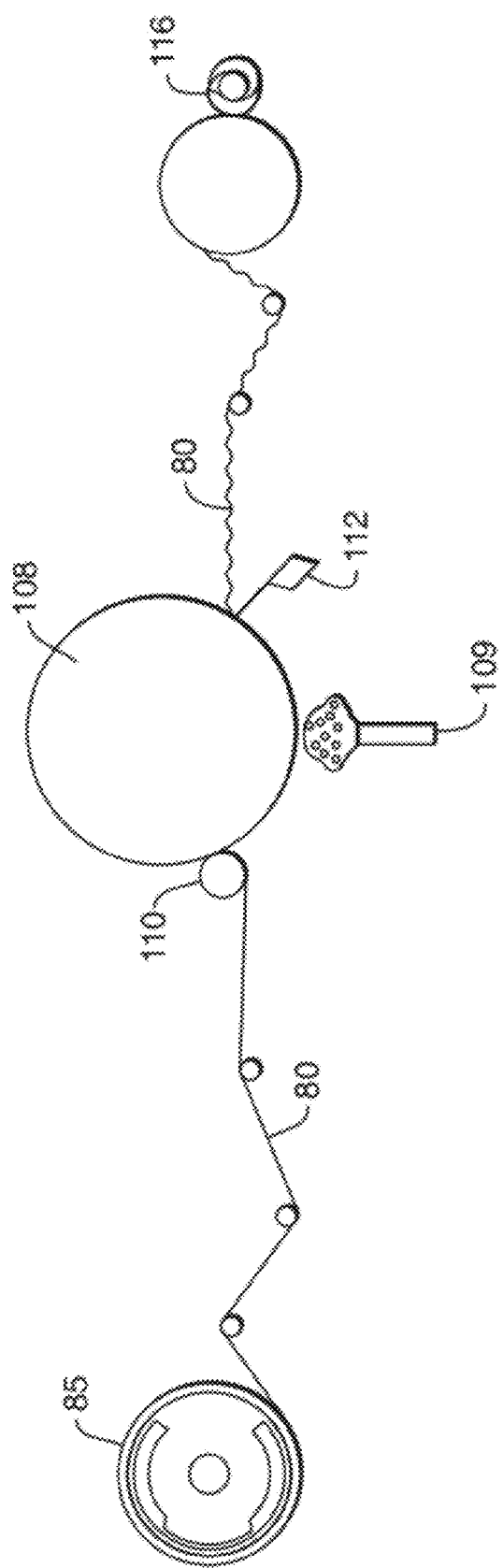
FIG. 3 is a side schematic view of an offline creping process according to one embodiment of the present invention, specifically showing froth application to the surface of a non-porous drum.
Figure 7:
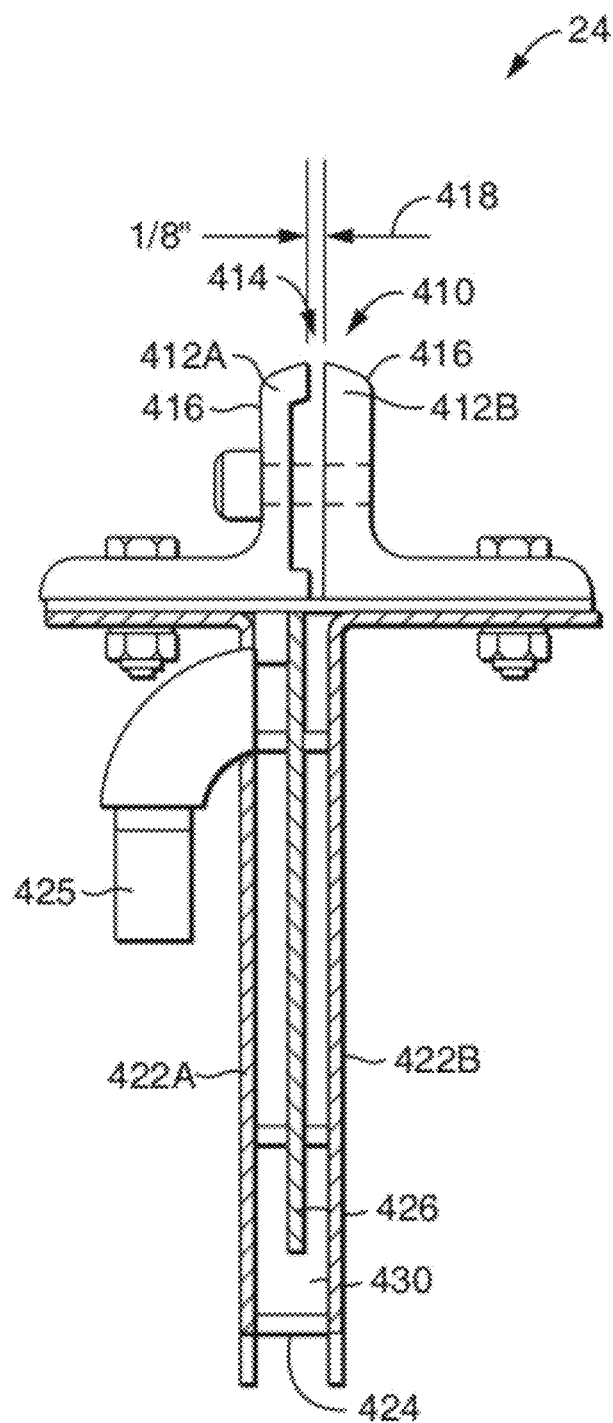
FIG. 7 is a side cross-section of a prior art parabolic chemical additive applicator.

Referring to FIGS. 2 and 7, it is most desirable to use a single parabolic applicator 24 to apply chemistry to a rotating dryer drum surface 23. However, if varying levels of chemical application are required across the width of the dryer surface due to dryer or basesheet variability, applicators (not shown) with multiple zones of miniature parabolic applicators may be used.

Referring to FIG. 7, shown is a cross-section of the parabolic applicator available from Gaston Systems, Inc., located in Stanley, N.C., U.S.A. Preferably, this parabolic applicator 24 is having the same applicator lip length as the width of the substrate. Generally, the parabolic applicator 24 has an applicator lip 410 constructed in part by two pieces of steel angle, 412A and 412B. These two pieces of steel angle define a slot opening 414 through which frothed chemicals can flow. As obtained from the manufacturer, the width 418 of slot opening 414 is 3.2 mm (⅛ inch), and the edges 416 of the steel angle applicator lip 410 are rounded to eliminate sharp edges.

Figure 8:
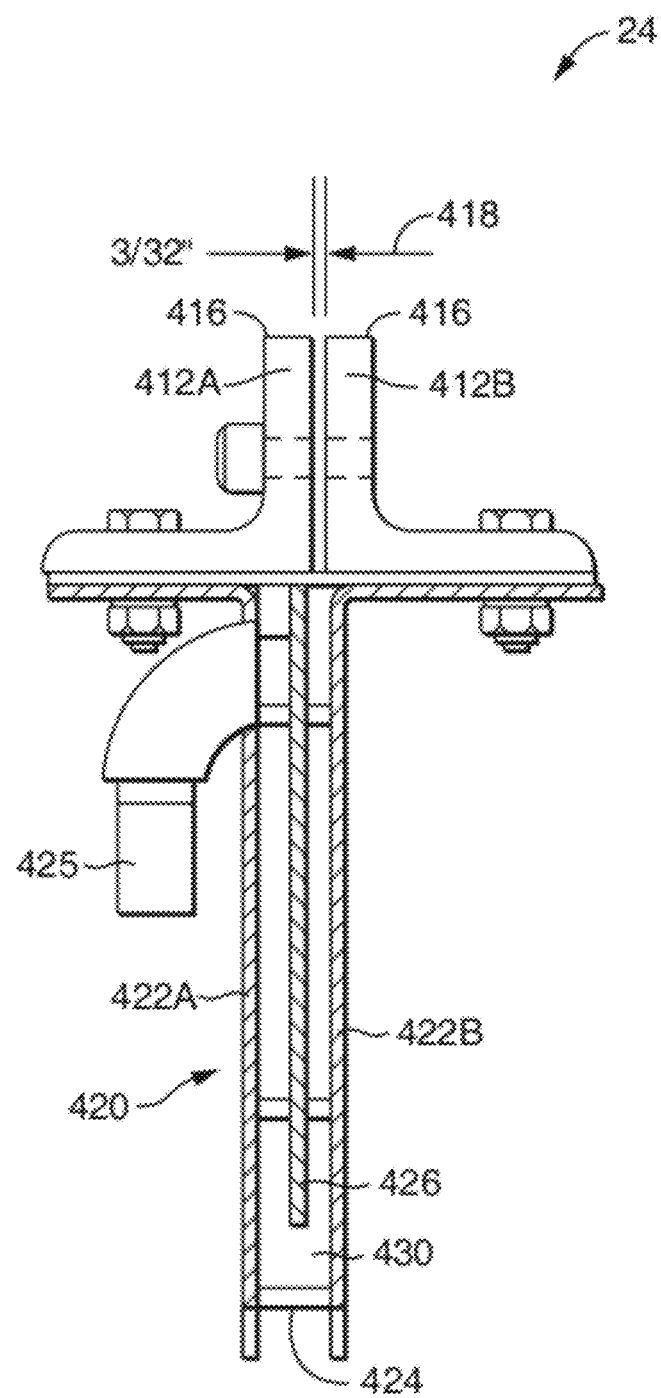
FIG. 8 is a side cross section of one parabolic chemical additive applicator according to one embodiment of the present invention.
Figure 9:
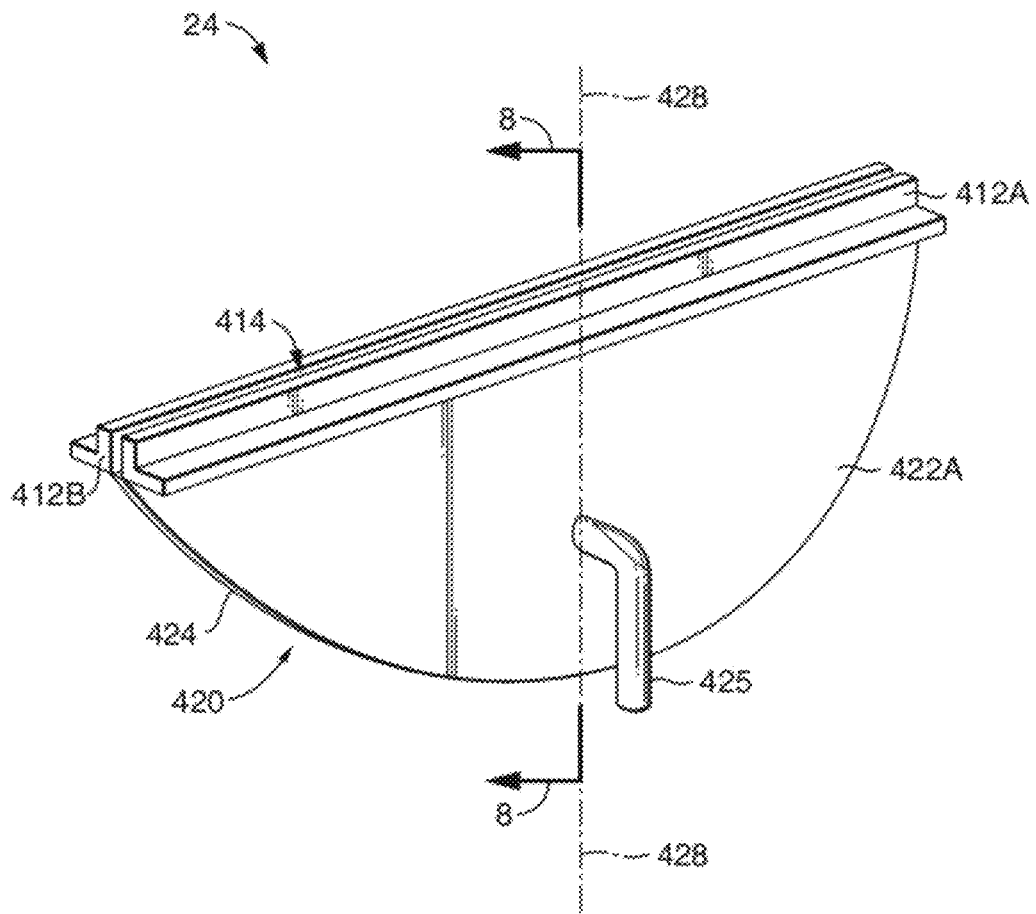
FIG. 9 is a front perspective view of the parabolic applicator shown in FIG. 8.

Referring to FIGS. 8 and 9, the complete applicator is shown. The applicator 24 includes a parabolic body 420. From the exterior, one can see that body 420 is constructed from two plates 422A and 422B which are joined to and separated by a side member 424. In addition, there is an inlet hose 425 desirably placed on along the symmetrical axis 428 of plate 422A. The inlet hose 425 may be adjacent to the steel angle 412A as seen in FIG. 8, or lower as seen in FIG. 9. Generally, the slot width 418 has been narrowed from 3.2 mm (⅛) inch to about 2.4 mm (3/32 inch). The narrower slot width 418 increases the foam velocity toward the intended surface (e.g. surface 23 of FIG. 1). Further, the edges 416 of the steel angle applicator lip 410 are squared, not rounded. The squared edges 416 increase the surface area of the applicator lip 410 which in turn increases the residence time the frothed chemicals have on the applicator lip 410. By increasing the residence time, the frothed chemistry has a greater tendency to attach to the dryer surface 23 as opposed to sliding down the applicator lip 410.

FIG. 8 shows that inside body 420 is a distribution plate 426. The purpose of the distribution plate 426 is to disperse the fluid entering the applicator 24 through inlet hose 25. The distribution plate has the same general shape as the plates 422, yet is smaller in size so that there remains a gap 430 between the distribution plate 426 and the side 424. Desirably the distribution plate 426 is equidistant from each of the plates 422A and 422B. Between the plate 422B and distribution plate 426 is a gap from which fluid can flow to the slot opening 414. Desirably, slot opening 414 is located symmetrically between the plate 422B and the distribution plate 426.

Figure 10:
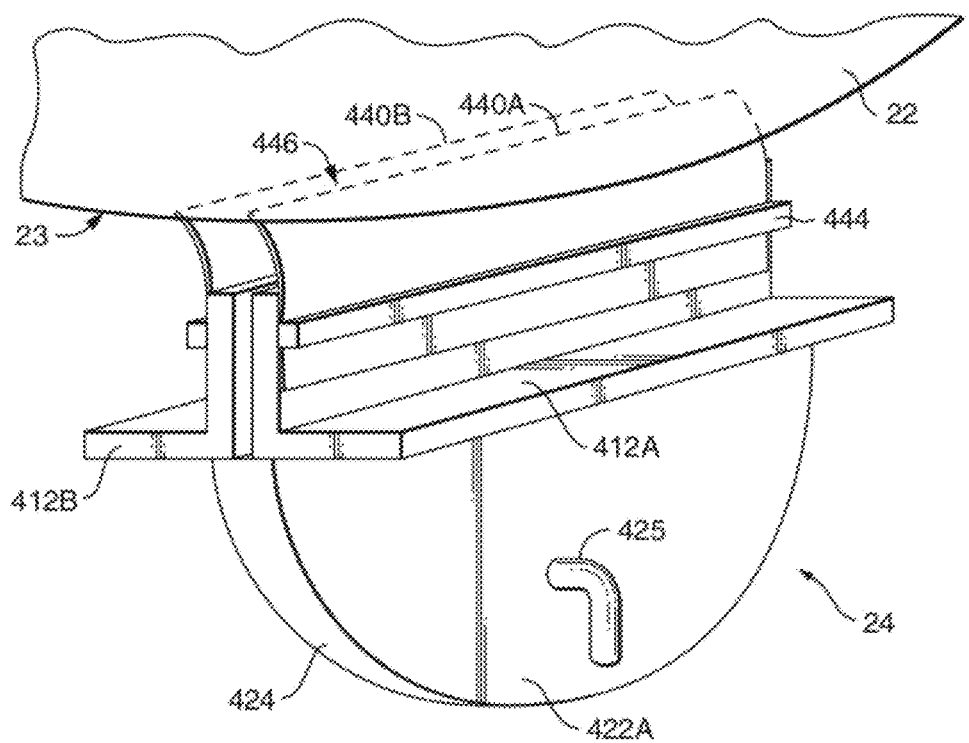
FIG. 10 is a front perspective view of the parabolic applicator of FIG. 9, modified to include wipes according to another embodiment of the present invention.

Referring to FIG. 10, in yet another embodiment, the purpose of felt wipes 440A and 440B (collectively referred to as felt wipes 440) is to spread a substantially uniform thickness of frothed additive composition on the dryer surface 23. This spreading action will result in a film of substantially uniform thickness. Desirably, the felt wipes 440 are approximately the same length as the steel angles 412A and 412B which define the length of slot opening 414. This will allow the frothed additive composition to be spread equally across the dryer surface 23. It is noted that the length of the steel angles 412A, B is larger than the length of the dryer surface that is aligned the dryer's rotational axis. The distance of felt wipes 440 between the applicator lip 410 and the felt wipe's outermost edge 446 may be between about 0.2 cm and about 50 cm. Desirably the rectangular felt wipes 440 are identical in size and shape. The thickness of each wipe may range between 0.125 mm and 25.4 mm, or desirably between 3.0 mm and 10 mm. Each of the felt wipes 440 are attached to a corresponding steel angle 412A and 412 B with a bar clamp 444. Desirably, fasteners such as metal screws (not shown) are spaced along the length of the bar clamp 444 for attachment to the steel angles. Desirably, the felt wipes 440 are made from polypropylene and Nylon fibers available from Albany International, located in Horner, N.Y., U.S.A. However, the felt wipe can be made from any other heat resistant sheet materials, such as metals, polymers (i.e. Teflon®), ceramic coated materials, natural based materials, etc.

Figure 11:
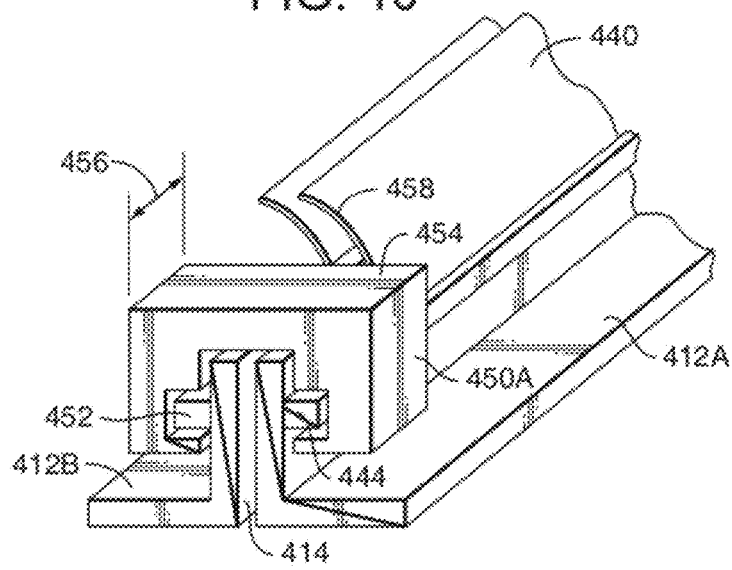
FIG. 11 is a partial side perspective view of the parabolic applicator of FIG. 10, modified to include end dams according to yet another embodiment of the present invention.

Referring to FIG. 11, in one embodiment, the applicator 24 is fitted with end dams 450, located on each side of the applicator lip. The end dams 450 are identical in shape and size, and are used to block frothed chemistry from flowing out in a cross-direction between the felt wipes 440. Each end dam is constructed from a material that is not negatively affected by the dryer heat and additive chemistry. Desirably, end dam 450 is a quasi-rectangular block in that one surface 454 shares the same curvature of the dryer surface 23, and an opposite surface that is slotted from side to side. The slot 452 is T-shaped as defined by the inner surface of the end dam 450. Specifically, the inner surface of end dam 450 is shaped so that it can slide over not only the steel angles 412A and 412B, but also, bar clamps 444.

As can be seen in FIG. 11, when end dams 450 are used, the steel angles 412A and 412B are extended beyond the felts 440 to at least the length corresponding to the end dam length 456. The end dams may be fastened into place by set screws. Further, the end dams are positioned against the edge of the felt wipes. Optionally, a shim (not shown) can be used to contain a flow of froth to the dryer surface and/or reinforce the felt wipes. Therefore, the shim(s) can be located next to the felt wipe(s) or in the place of the felt wipe(s).

Figure 12:
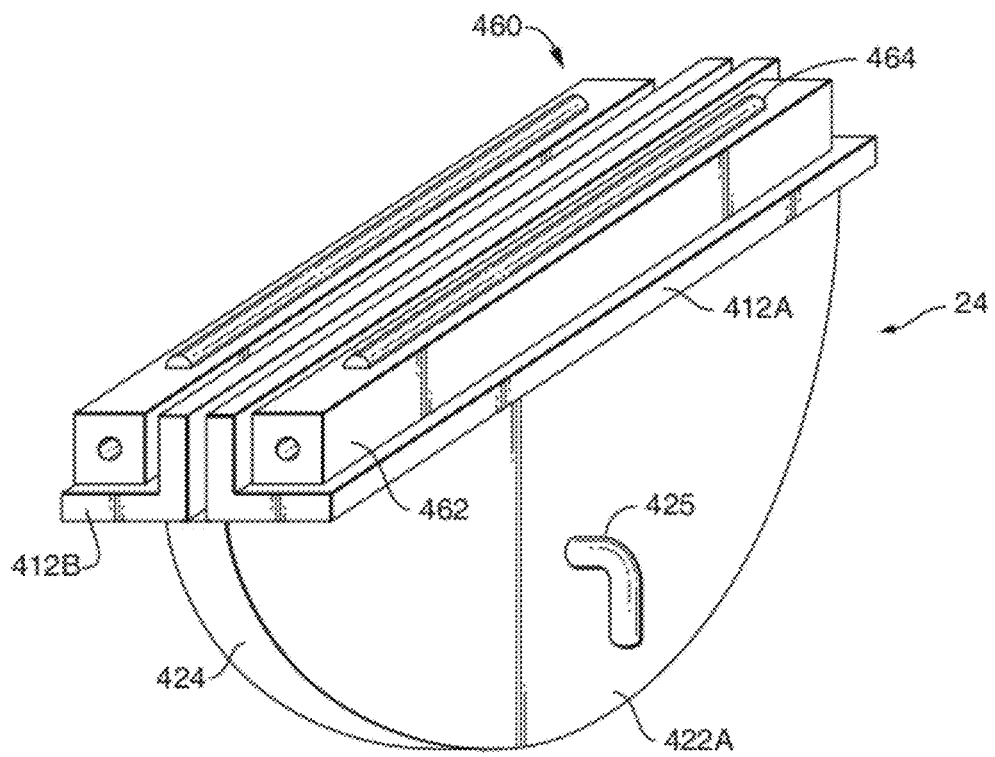
FIG. 12 is a front perspective view of the parabolic applicator of FIG. 9, modified to include rollers according to a further embodiment of the present invention.
Figure 13:
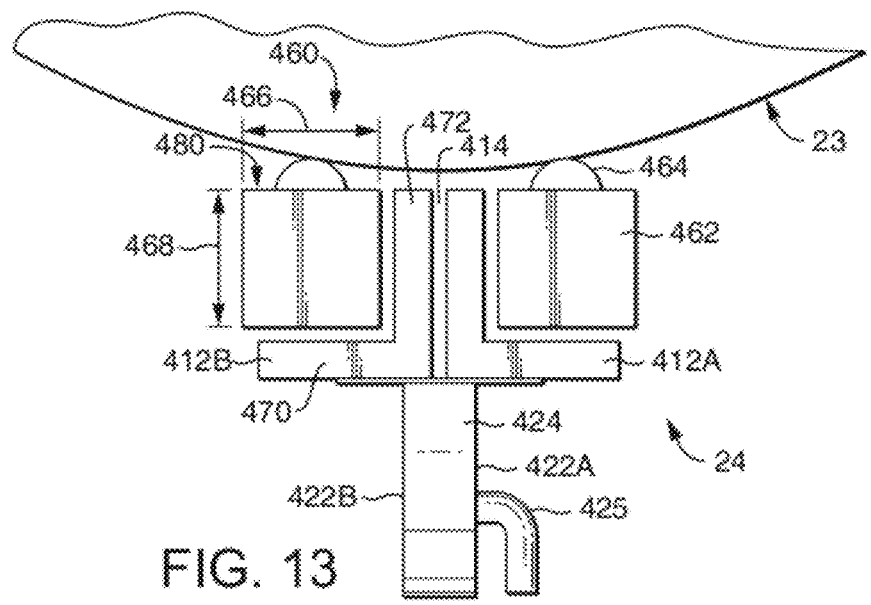
FIG. 13 is a partial side elevation of the parabolic applicator of FIG. 12.

Referring now to FIGS. 12 and 13, in one embodiment of the present invention, rollers 460 are used to minimize overflow of froth coming from applicator 24. The rollers 460 include a roller casing 462 and a roller member 464. The roller casing 462 is an elongated rectangular tube that has a width 466 that fits against the lower arm 470 of a steel angle 412 (e.g. 412B) and has a height that is flush with the applicator lip (upper arm 472 of a steel angle 412). In the uppermost face 480 of each casing 462 is a slot that is dimensioned to allow the roller member 464 to partially protrude so that it may be placed in contact with the dryer 23 surface. Generally, the roller members 464 are longer than the width of the substrate. When placed against the dryer 23 surface, the roller member 464 creates a barrier that prohibits the overflow of froth coming from the applicator 24. The roller member 464, being in contact with the dryer 23, is driven by the rotational speed of the dryer 22.

Figure 16:
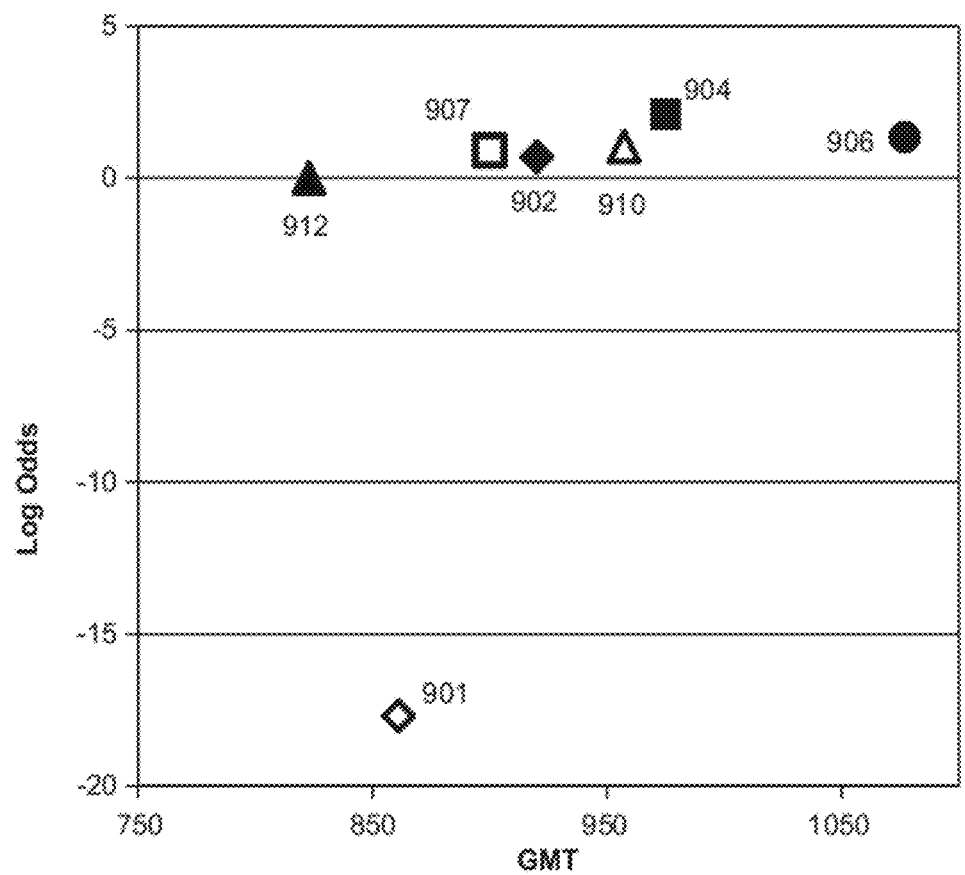
FIG. 16 is a graph plotting GMT vs. Log Odds for softness of the 2 ply facial tissue products comprising a combination benefit agent of the present invention.

FIG. 16 plots a graph showing the GMT vs. Log Odds for softness of a 2 ply facial tissue product using raw tissue sheets from Table 16 of Example 9. The difference in log odds between the control code and all frothed and surface treated codes with the benefit agents of this invention is surprisingly large at close to 18 log odds or more. All had higher GMTs than the control code (Code 901), except the code with both the cotton and expandable bead additions (Code 912) which was comparable in strength. The code with silica gel particles (Code 906) demonstrated a much high GMT value than all the codes at a parity softness with the other codes with the benefit agents. This means that this code provides higher softness values at parity GMT strengths, which is one of the benefits of using an enhancement component. The codes with the enhancement components (Codes 904-912) have also demonstrated novel hand feel beyond what the log odds softness value can illustrate. In general, the enhancement component makes the additive composition coating (i.e., the ocean layer) exhibit a novel and improved hand feel. For example, Code 902 demonstrates the use of HYPOD 8510® as an additive composition and is frothed/surface coated onto a substrate without an enhancement component. When its surface is touched, it provides significant softness improvement in comparison to the same tissue with conventional creping chemistry (i.e., Code 901). However, at the same time, it also feels slightly waxy or slippery. Some types of consumers may like this slippery feel, but others may not want to have the feel. Adding an enhancement component can change the feel without compromising the softness improvement. The hand feel obtained through this approach includes, but is not limited to, cottony, velvety, fluffy, and/or hairy. Another benefit of adding the enhancement component(s) is that the additive composition HYPOD 8510® coating layer has an improved strength which was important when the benefit agents were applied onto pre-prepared substrates, such as thermoplastic nonwovens. This improved strength enables the coated film of the benefit agents to have a uniform and complete coverage on the substrate.

Additionally, it was shown that enhancement components and the method of application could be used to enhance surface feel, such as softness or improve surface properties, such as absorbency, friction, bulk, etc. Additionally, other surface benefits, such as scents, anti-bacterial, moisturizing, soothing agents, etc., could be applied better than the additive composition HYPOD 8510® alone could provide. The code comprising both HYPOD 8510® and polyvinylpyrrolidone-styrene was perceived to be almost 1.5 log odds softer (significant) than the HYPOD 8510® code (Code 902) without any enhancement components.

Applicants found that the IHR results for the HYPOD 8510® frothed code with 6% silica gel particles as the enhancement components resulted in having the softest perceived results with a greater than 5 log-odds difference from the non-frothed code with conventional creping chemistry. The HYPOD 8510® frothed control without any enhancement components was next at over 4 log-odds difference. All other frothed codes were perceived to be at least 3 log odds softer than the control non-frothed code.

Figure 17:
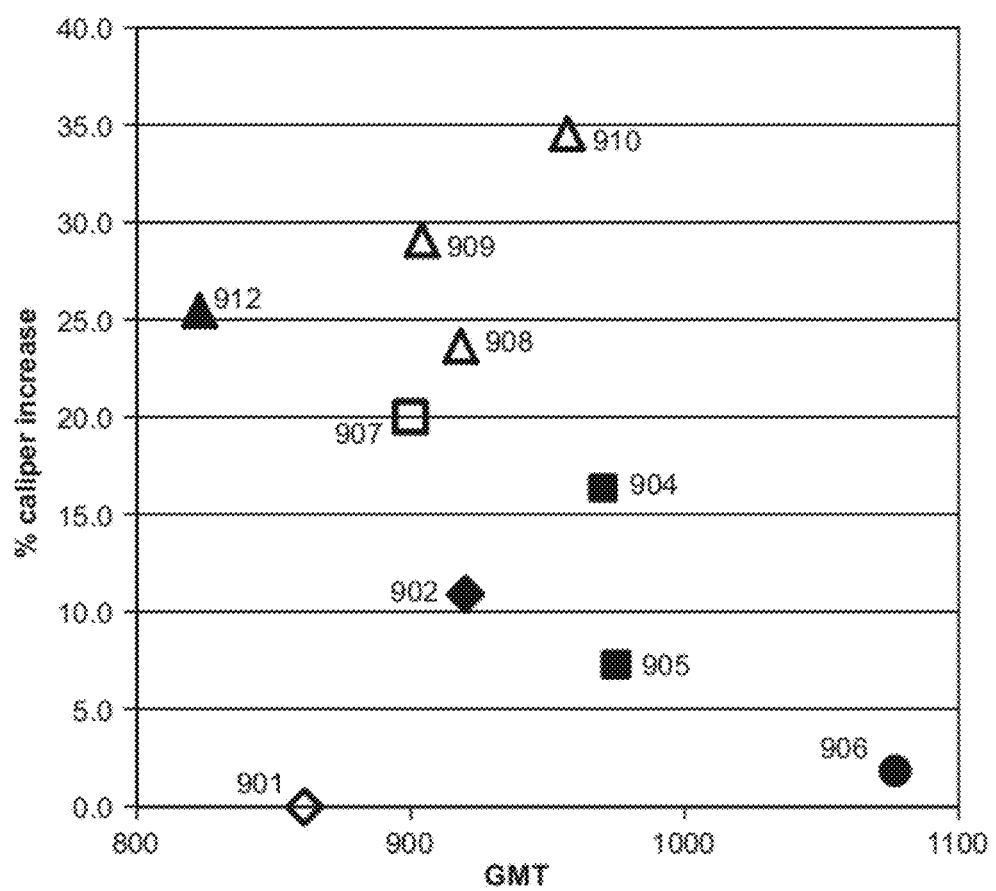
FIG. 17 shows a graph plotting GMT vs. increased caliper of the 2 ply facial tissue products comprising a combination benefit agent of the present invention.

Another benefit to adding enhancement components is the tremendous caliper increase that can be achieved while generally maintaining or having greater tensile strength than the non-frothed surface treated code. These codes were all calendered at the same nip pressure for the facial converting process. The percentages listed next to the data points are the amounts of the enhancement components added based on HYPOD 8510®dry weight in the formulation before frothing. In FIG. 17, all the frothed and creped codes showed an added increase in bulk over the non-frothed and creped code (Code 901) with the highest level increases at almost 35%. The majority of the codes with the enhancement components increased bulk over the frothed code comprising only HYPOD 8510® (Code 902). All of the processing conditions, such as blade types, bevel, and pressure loadings, were the same.

Creping Process

Creping is part of the substrate manufacturing process wherein the substrate is scraped off the surface of a rotating dryer (e.g. a Yankee Dryer) via a blade assembly. Shown in FIG. 3 is a simple example of the application of a benefit agent being applied as part of an offline creping process. An applicator 109 applies the frothed benefit agent of the present invention to the surface of the dryer drum 108. Applicator 109 may be positioned at the bottom of the dryer drum 22. For example, the applicator 109 may be at a "six o-clock", "twelve o-clock", "three o-clock", or "nine o-clock" position. The applicator lip should be positioned as close to or touching the dryer surface to allow the frothed chemicals to come in contact to the dryer surface 23.

From the tissue roll 85, a dried tissue web 80 proceeds toward the dryer drum 108 for conversion to a coated tissue. A press roll 110 provides the needed pressure for adhering web 85 to the outer surface of dryer 108. The additive composition adheres the tissue web 80 to the surface of the dryer drum 108. The additive composition is transferred to the tissue web as the web is creped from the drum using a creping blade 112. Once creped from the dryer drum 108, the tissue web 80 is wound into a roll 116.

EXAMPLES

The following examples further describe and demonstrate embodiments within the scope of the present invention. The examples are given solely for the purpose of illustration and are not to be construed as limitations of the present invention, as many variations thereof are possible without departing from the spirit and scope of the invention.

Example 1

In this example, three dry substrates were used: 54 gsm hydroentangled material (85% cellulose and 15% spunbond), obtainable from Kimberly-Clark Professional®, WYPALL X®-50 hydroentangled wipers, 42 gsm UCTAD bath tissue and 17 gsm facial tissue. (The facial tissue base sheets were not run up to 1000 fpm.) The dry substrates were treated in an offline creping process.

A commercial HYPOD 8510® dispersion was diluted to a solid level by mill water that was pre-treated by the addition of $Na_2CO_3$ at a level of 2 g per 10 kg water, and then frothed by a Gaston CFS 10 inch Foam Generator. In some aspects, a foaming agent was used. One foaming agent is hydroxypropyl cellulose which serves to enhance froth stability. This material may be available from Ashland, Inc., Wilmington, Del., U.S.A, and is sold under the KLUCEL® brand. The stable froth was applied onto a hot Yankee dryer surface and then directly bonded with the dry substrate by a pressure roll.

The treated substrate was then scraped off the Yankee dryer surface after the froth cured. Curing should take place in the time defined by the machine speeds listed in Table 1. The Yankee dryer had a diameter of 72 inches and heated to a surface temperature of about 300° F.

TABLE 1

| | | Coating Composition (g/10 kg dispersion)** | | | Foam Unit Settings | | | Process Parameter | |
|---|---|---|---|---|---|---|---|---|---|
| | | | | | Flow Rate | Mixing | Blow | Yankee Temp. | Machine Speed |
| Code | Substrate | HYPOD | KLUCEL* | $Na_2CO_3$ | (l/min) | (%) | Ratio | (° F.) | (ft/min) |
| 1 | HYDROKNIT | 4762 | 50 | 2 | 1000 | 50 | 15 | 300 | 500 |
| 2 | HYDROKNIT | 4762 | 50 | 2 | 1000 | 50 | 15 | 300 | 750 |
| 3 | HYDROKNIT | 4762 | 0 | 2 | 1000 | 50 | 15 | 300 | 1000 |
| 4 | UCTAD | 4762 | 0 | 2 | 1000 | 50 | 15 | 300 | 250 |
| 5 | UCTAD | 4762 | 0 | 2 | 1000 | 50 | 15 | 300 | 500 |
| 6 | UCTAD | 2381 | 0 | 2 | 1000 | 50 | 15 | 300 | 500 |
| 7 | UCTAD | 4762 | 0 | 2 | 1000 | 50 | 15 | 300 | 750 |
| 8 | UCTAD | 2381 | 0 | 2 | 1000 | 50 | 15 | 300 | 1000 |
| 9 | UCTAD | 4762 | 0 | 2 | 1000 | 50 | 15 | 300 | 1000 |
| 10 | Facial Tissue | 2381 | 0 | 2 | 1000 | 50 | 15 | 300 | 50 |

*HYPOD ® is a 42 wt % aqueous dispersion from Dow and KLUCEL ® is hydroxypropyl cellulose available from Ashland, Inc. with a designation of K.

**Water will be added to make up to 10 kg dispersion.

Example 2

In this group of samples, dry UCTAD tissue with a basis weight of 42 gsm was treated in an offline creping process. Coating chemistries were diluted to different solid levels by mill water that was pre-treated by addition of $Na_2CO_3$ at a level of 2 g per 10 kg water. The dilution was then frothed by the Gaston foam generator. The froth was applied onto hot Yankee dryer surface of (the same dryer of Example 1) and then bonded to the dry UCTAD sheet by a pressure roll. The treated UCTAD sheets were then scraped off the Yankee dryer surface after the add-ons were cured at a temperature listed in Table 2.

TABLE 2

| | | Coating Composition | | | | Foam Unit Settings | | |
|---|---|---|---|---|---|---|---|---|
| | | (g/10 kg dispersion)*** | | | | Flow | | |
| | | DPOD | | | | Rate | Mixing | Blow |
| Code | Substrate | Type* | Amount | KLUCEL** | $Na_2CO_3$ | (ml/min) | (%) | Ratio |
| 1 | UCTAD | HYPOD | 7142 | 0 | 2 | 1000 | 50 | 10 |
| 2 | UCTAD | HYPOD | 4762 | 0 | 2 | 1000 | 50 | 10 |
| 3 | UCTAD | HYPOD | 2381 | 0 | 2 | 1000 | 50 | 10 |
| 4 | UCTAD | HYPOD | 1190 | 0 | 2 | 1000 | 50 | 10 |
| 5 | UCTAD | HYPOD | 1190 | 25 | 2 | 1000 | 50 | 10 |
| 6 | UCTAD | HYPOD | 595 | 0 | 2 | 1000 | 50 | 10 |
| 7 | UCTAD | HYPOD | 595 | 12.5 | 2 | 1000 | 50 | 10 |
| 8 | UCTAD | 80/20 | 5454 | 0 | 2 | 1000 | 50 | 10 |
| 9 | UCTAD | 80/20 | 3636 | 0 | 2 | 1000 | 50 | 10 |
| 10 | UCTAD | 80/20 | 1818 | 0 | 2 | 1000 | 50 | 10 |
| 11 | UCTAD | 80/20 | 909 | 0 | 2 | 1000 | 50 | 10 |

| | Process Parameter | |
|---|---|---|
| | Yankee Temp. | Machine Speed |
| Code | (° F.) | (ft/min) |
| 1 | 300 | 50 |
| 2 | 300 | 50 |
| 3 | 300 | 50 |
| 4 | 300 | 50 |
| 5 | 300 | 50 |
| 6 | 300 | 50 |
| 7 | 300 | 50 |
| 8 | 300 | 50 |
| 9 | 300 | 50 |
| 10 | 300 | 50 |
| 11 | 300 | 50 |

(Referring to Table 2)

Note:

*HYPOD 8510 ® contains 60% AFFINITY ® and 40% PRIMACOR ®; the 80/20 chemistry contains 80% AFFINITY ® and 20% PRIMACOR ®, with a solid level of 55 wt % and a viscosity around 100 cps.

**KLUCEL ® is hydroxypropyl cellulose available from Ashland, Inc., with a designation of K.

***Water will be added to make up to 10 kg dispersion.

Example 3

This is the first example that demonstrates the feasibility of frothed chemistry on a pilot tissue machine that operates at a speed that is near that of a commercial tissue machine. Two additive compositions were tried: (1) a creping chemistry made with CREPETROL 870® (90 percent) and CREPETROL® 874 (10 percent): it is 25% solid liquid and available from Ashland, Inc. located in Wilmington, Del., U.S.A., and (2) commercial polyolefin dispersion, HYPOD 8510®, a 42% solid dispersion available from the Dow Chemical Company. The dispersion had about 1 micron average particle size, melting point of 63 C, and a glass transition of −53. Both chemistries were frothed before applied onto hot Yankee dryer surface. The dryer has a diameter of 96 inches. A foaming agent, UNIFROTH 0800, a 38% solid liquid, available from UniChem Inc., was used to stabilize the frothed dispersions of the above two.

TABLE 3

| | | Coating Composition ||||| Froth Unit Settings |||
| | | Coatings |||| | | | |
| Code | Facial Tissue Composition | Creping Chemistry (liter) | HYPOD (liter) | UNIFROTH 0800* (liter) | Water (liter) | Flow Rate (ml/min) | Mixing (%) | Blow Ratio |
|---|---|---|---|---|---|---|---|---|
| 1 | 70% Euc/ 30% Pictou | 17.01 | | 2.45 | 75.04 | 300 | 50 | 10 |
| 2 | 70% Euc/ 30% Pictou | | 10.8 | 2.32 | 77.6 | 300 | 50 | 10 |
| 3 | 70% Euc/ 30% Pictou | | 10.8 | 2.32 | 77.6 | 150 | 50 | 20 |
| 4 | 70% Euc/ 30% Pictou | | 10.8 | 2.32 | 77.6 | 150 | 50 | 15 |
| 5 | 70% Euc/ 30% Pictou | | 10.8 | 2.32 | 77.6 | 150 | 50 | 10 |
| 6 | 70% Euc/ 30% Pictou | | 10.8 | 2.32 | 77.6 | 100 | 50 | 8 |
| 7 | 70% Euc/ 30% Pictou | | 10.8 | 2.32 | 77.6 | 100 | 50 | 8 |

| | Process Parameter ||
| Code | Yankee Temp (° F.) | Machine Speed (ft/min) |
|---|---|---|
| 1 | 550 | 2000 |
| 2 | 550 | 2000 |
| 3 | 550 | 2000 |
| 4 | 550 | 2000 |
| 5 | 550 | 2000 |
| 6 | 550 | 2000 |
| 7 | 550 | 2000 |

Note:
*UNIFROTH 0800 ® is an anionic surfactant with a solid level of 38% available from UniChem Inc.

Example 4

In this example, dry substrates were used and treated in an offline creping process. Commercial HYPOD 8510® dispersion was diluted with mill water to a solid level which was pre-treated by addition of $Na_2CO_3$ at a level of 2 g per 10 kg water and then frothed by the Gaston unit, supra. The stable froth was applied to the hot drum surface of the 72 inch Yankee dryer and adhered to the dry substrate with a pressure roll. The treated substrates were then scraped off the Yankee surface after the chemistries were cured for the times and temperatures listed in Table 4. Three dry substrates were used in this example: Spunbond and BCW nonwovens, and a 42 gsm UCTAD tissue. The spunbond is made of a bicomponent, fiber and has a basis weight of 18 gsm. The BCW, has a basis weight of 20 gsm. The bicomponent fiber may be a PP/PE (Polypropylene/Polyethylene) side-by-side spunbond bicomponent fiber. See for example U.S. Pat. No. 5,382,400, incorporated herein to the extent it does not conflict with the present invention.

TABLE 4

| | | Coating Composition | | | Froth Unit Settings | | |
|---|---|---|---|---|---|---|---|
| | | Coatings | | HYPOD | Water | Flow Rate | Mixing | Blow |
| Code | Substrates | Type | Solids | (kg) | (kg) | (ml/min) | (%) | Ratio |
| 1 | Spunbond | HYPOD | 30% | 26.5 | 10.6 | 300 | 30 | 10 |
| 2 | Spunbond | HYPOD | 20% | 18.9 | 20.8 | 300 | 50 | 8 |
| 3 | Spunbond | HYPOD | 10% | 7.5 | 24.2 | 300 | 50 | 8 |
| 4 | BCW | HYPOD | 30% | 26.5 | 10.6 | 300 | 30 | 10 |
| 5 | BCW | HYPOD | 20% | 18.9 | 20.8 | 300 | 35 | 10 |
| 6 | BCW | HYPOD | 10% | 7.5 | 24.2 | 300 | 50 | 10 |
| 7 | UCTAD | HYPOD | 30% | 26.5 | 10.6 | 300 | 30 | 10 |
| 8 | UCTAD | HYPOD | 20% | 18.9 | 20.8 | 300 | 35 | 10 |
| 9 | UCTAD | HYPOD | 10% | 7.5 | 24.2 | 300 | 50 | 10 |

| | Process Parameter | |
|---|---|---|
| Code | Yankee Temp. (° F.) | Machine Speed (ft/min) |
| 1 | 250 | 50 |
| 2 | 280 | 50 |
| 3 | 300 | 50 |
| 4 | 250 | 50 |
| 5 | 250 | 50 |
| 6 | 300 | 50 |
| 7 | 250 | 50 |
| 8 | 250 | 50 |
| 9 | 300 | 50 |

Example 5

In this example, coating chemistries were frothed and applied onto the drum of a Yankee dryer in an inline fashion. The dryer had a diameter of 24 inches. Using a pressure roll, the film resulting from applying the frothed add-on to the dryer was then contacted with the wet cellulose pulp sheet having a consistency of around 40% solids by weight.

There were four different pulps used in this example. Two pulps were the same as that used to make a Kimberly-Clark standard facial tissue: Eucalyptus and Pictou fiber (Northern soft wood kraft), while other two pulps were of lower comparative cost and quality: Southern Alabama Pine (SAP) and SFK recycled fiber available from SFK Pulp Recycling U.S. Inc.

In general, facial tissue produced from the lower cost pulp tends to have less softness. It is desirable to use a HYPOD 8510® surface coating to make a low cost pulp tissue product that has parity or even improved softness as a standard facial tissue made with conventional creping chemistry.

The wet sheet with different combinations of the different pulps was dried on the hot Yankee surface together with the additive chemistry and then scraped off the drum surface. Samples 1 to 3 are not surface coated with the frothed chemicals. Sample 1 was a control facial tissue produced in the same way as a Kimberly-Clark® standard facial tissue product. Samples 2 and 3 were control samples for low cost pulp facial tissues which were produced in the same way as a Kimberly-Clark® standard facial tissue. All of the control samples were produced by spraying unfrothed creping chemistries onto the dryer drum. The creping chemistry was prepared by mixing 2500 ml of 6% polyvinyl alcohol, 100 ml of 12.5% KYMENE®, and 15 ml of 7.5% REZOSOL® in 25 gallons of mill water.

For examples 4 through 9, HYPOD 8510® was diluted to different levels of solids and mixed with additional foaming agent, either KLUCEL® or UNIFROTH 0800®, before each dispersion was frothed by the Gaston foam generator (supra) and applied onto the dryer for the surface coating treatment.

TABLE 5

| Code | Facial Tissue Composition | Coating Composition g/10 kg dispersion)* | | | | Foam Unit Settings | | | Tissue |
|---|---|---|---|---|---|---|---|---|---|
| | | HYPOD | KLUCEL | UNIFROTH 0800 | $Na_2CO_3$ | Flow Rate (ml/min) | Mixing (%) | Blow Ratio | GMT (gf) |
| 1 | 70% Euc/30% Pictou | NA | NA | NA | NA | NA | NA | NA | 809 |
| 2 | 70% Euc/30% SAP | NA | NA | NA | NA | NA | NA | NA | 941 |
| 3 | 75% SFK/25% Euc | NA | NA | NA | NA | NA | NA | NA | 771 |
| 4 | 70% Euc/30% Pictou | 1190 | 0 | 65.8 | 0 | 180 | 50% | 25 | 620 |
| 5 | 70% Euc/30% Pictou | 1190 | 0 | 65.8 | 0 | 150 | 50% | 25 | 573 |
| 6 | 70% Euc/30% Pictou | 595 | 0 | 65.8 | 2 | 180 | 50% | 25 | 672 |
| 7 | 70% Euc/30% Pictou | 595 | 6 | 0 | 2 | 150 | 50% | 25 | 644 |
| 8 | 70% Euc/30% SAP | 595 | 6 | 0 | 2 | 180 | 50% | 25 | 632 |
| 9 | | 595 | 6 | 0 | 2 | 150 | 50% | 25 | 692 |

| Code | Process Parameter | |
|---|---|---|
| | Sheet Temp (° F.) | Machine Speed (ft/min) |
| 1 | 239 | 60 |
| 2 | 237 | 60 |
| 3 | 237 | 60 |
| 4 | 260 | 60 |
| 5 | 259 | 60 |
| 6 | 259 | 60 |
| 7 | 259 | 60 |
| 8 | 259 | 60 |

Note:
*Water will be added to make up to 10 kg dispersion

Example 6

In this example, dry substrates were used and treated in an offline creping process. The Yankee dryer had a diameter of 72 inches. There were two groups of coating chemistries used in this study: dispersions and solutions. Table 6 summarizes the group of water soluble solution chemistries and mixture solution solids levels. For this group, we had to pre-dissolve each add-on to form a solution, and then prepare mixtures from each solution. The commercial HYPOD 8510® dispersion was also diluted to different solid levels. The solutions and dispersions prepared were frothed by the Gaston foam generating unit and applied onto the hot dryer drum surface.

The resulting film then contacted the dry substrate by a pressure roll. The treated substrates were then scraped off the Yankee surface after the chemistries were cured for certain time at temperatures listed in Table 7. Four dry substrates were used in this group: 18 gsm Spunbond, 42 gsm UCTAD bath tissue, and 14.1 gsm facial tissue.

Table 6 contains information of two types of polymer solutions: five pre-prepared solutions listed on the left side of the table, and three mixtures of the pre-prepared solutions. These three mixtures are R1, R2 and R3. For example, R1 is a mixture solution prepared by mixing three pre-prepared solutions (45% of pre-prepared 10% glucosol, 40% of pre-prepared 40% PEG, and 15% of pre-prepared 2% Polyox). The mixture solution has a solid level of 20.8% which is resulted from the equation of 45%*10%+40%*40%+15%*2%=20.8%. Mixture solids for R2 and R3 are calculated the same way as the R1's.

TABLE 6

| Pre-prepared Solutions (wt %) | | Mixture of Solutions (wt %) | | |
|---|---|---|---|---|
| Polymer Type | Solids | R1 | R2 | R3 |
| Glucosol: hydroxypropyl starch | 10% | 45% | 65% | 40% |
| PEG: polyethylene glycol | 40% | 40% | | |
| Polyox: polyethylene oxide | 2% | 15% | | |
| HEC: hydroxyethyl cellulose | 2% | | 35% | |
| PVOH: polyvinyl alcohol | 6% | | | 25% |
| HYPOD | 42% | | | 35% |
| Mixture Solids | | 20.8% | 7.2% | 20.2% |

TABLE 7

| | | Coating Composition | | | Froth Unit Settings | | |
|---|---|---|---|---|---|---|---|
| | | | g/10 kg dispersion | | Flow | | |
| | | Coatings | | UNIFROTH | Rate | Mixing | Blow |
| Code | Substrates* | Type | Solids | KLUCEL | 0800 | (ml/min) | (%) | Ratio |
| 1 | Spunbond | HYPOD | 8333 | 0 | 0 | 250 | 30 | 7 |
| 2 | Spunbond | HYPOD | 8333 | 0 | 0 | 250 | 30 | 7 |
| 3 | Spunbond | HYPOD | 4762 | 0 | 0 | 300 | 30 | 10 |
| 4 | Spunbond | HYPOD | 2381 | 0 | 0 | 200 | 30 | 15 |
| 5 | Spunbond | HYPOD | 595 | 14.8 | 0 | 200 | 30 | 15 |
| 6 | Spunbond | HYPOD | 2381 | 0 | 0 | 300 | 30 | 15 |
| 7 | Spunbond | HYPOD | 2381 | 0 | 0 | 200 | 30 | 15 |
| 8 | Spunbond | HYPOD | 595 | 14.8 | 0 | 200 | 30 | 15 |
| 9 | UCTAD | HYPOD | 4762 | 0 | 0 | 250 | 30 | 7 |
| 10 | UCTAD | HYPOD | 595 | 14.8 | 0% | 300 | 30 | 10 |
| 11 | Facial | R1 | 2403 | 0 | 526 | 150 | 40 | 15 |
| 12 | Facial | R2 | 2083 | 0 | 526 | 150 | 40 | 15 |
| 13 | Facial | R3 | 2357 | 0 | 0 | 300 | 40 | 5 |

| | Process Parameter | | |
|---|---|---|---|
| | Temp. (° F.) | | Machine Speed |
| Code | Dryer | Sheet | (ft/min) |
| 1 | 265 | 220 | 50 |
| 2 | 265 | 203 | 200 |
| 3 | 265 | | 50 |
| 4 | 265 | 198 | 50 |
| 5 | 270 | 214 | 50 |
| 6 | 270 | 209 | 250 |
| 7 | 280 | 224 | 50 |
| 8 | 280 | 218 | 50 |
| 9 | 265 | 245 | 50 |
| 10 | 250 | 230 | 50 |
| 11 | 270 | 228 | 50 |
| 12 | 290 | 257 | 50 |
| 13 | 285 | 250 | 50 |

Example 7

A modification of froth applicator was made as described above. All such changes were intended to enhance the froth vertical velocity. This will reduce the probability that the froth will run off of the applicator's lip and not onto the dryer surface. One advantage of such a modification is to enable of the use of a lower flow rate to reduce the amount of coating without lowering the solids level.

A lower amount of the additive composition may be achieved by reducing the HYPOD 8510® solid levels. HYPOD 8510® was diluted to a solid level of 5% or lower so that lower levels of additive composition were disposed on the tissue substrate. However, as mentioned above, the unique microporous structure of the froth is formed largely due to high viscosity and high solids of coating chemistries. The modification of the applicator allows the reduction of additive composition levels on the tissue without compromising the formation of the unique frothed tissue structure of the present invention. The samples of Table 8 summarize the operating conditions used with the modified applicator. Codes 1 and 2 were made with a conventional creping chemistry listed in Example 5. Codes 3-7 were made with frothed HYPOD 8510®.

TABLE 8

| | | Coating Composition | | Foam Unit Settings | | | |
| --- | --- | --- | --- | --- | --- | --- | --- |
| Code | Facial Tissue Composition | HYPOD | Amount (g/10 kg dispersion) | Flow Rate (ml/min) | Mixing (%) | Blow Ratio | Tissue GMT (gf) |
| 1 | 70% Euc/ 30% Pictou | NA | NA | NA | NA | NA | 812 |
| 2 | 100% recycled fiber RFK | NA | NA | NA | NA | NA | 844 |
| 3 | 70% Euc/ 30% Pictou | 8510 | 7143 | 100 | 50 | 12 | 911 |
| 4 | 70% Euc/ 30% Pictou | 8510 | 7143 | 100 | 30 | 6 | 835 |
| 5 | 100% recycled fiber RFK | 8510 | 7143 | 100 | 30 | 6 | 978 |
| 6 | 100% recycled fiber RFK | 8510 | 4762 | 100 | 30 | 5 | 1001 |
| 7 | 70% Euc/ 30% Pictou | 8510 | 4762 | 100 | 30 | 6 | 900 |

| | Process Parameter | |
| --- | --- | --- |
| Code | Sheet Temp. (° F.) | Machine Speed (ft/min) |
| 1 | 239 | 60 |
| 2 | 239 | 60 |
| 3 | 257 | 60 |
| 4 | 257 | 60 |
| 5 | 257 | 60 |
| 6 | 260 | 60 |
| 7 | 257 | 60 |

Pictou is classified as Northern soft wood kraft pulp.

RFK is 100% recycled fiber grade available from SFK (supra).

Sensory Panel Evaluation Results:
Study I:

This study was performed to determine softness per the In-Hand Ranking Test for Tactile Properties (IHR test). In this study, four tissue materials were selected. The following codes from Example 1 were tested: untreated facial and UCTAD bath tissues, a facial tissue treated with HYPOD (code 10, Table 1), and UCTAD tissues (code 8, Table 1). Each facial tissue code was a 2-ply facial tissue with either (1) the coated surface (also the creped side) facing outside so that the user can only touch the softer and smoother side. One-ply UCTAD tissue was also tested, but only has one creped side in accordance with the present invention. The IHR test only uses the treated side(s).

Table 9 summarizes the four codes that were the subjects of this study. The tissue content of HYPOD was determined by measuring the potassium content of the tissue samples versus the HYPOD dry polymer potassium content. (The HYPOD PRIMACOR component is potassium polyacrylate).

TABLE 9

| | | HYPOD Content | |
|---|---|---|---|
| Code | Description | (%) | mg/m² |
| Control facial | 14 gsm 2 ply facial tissue | 0 | 0 |
| HYPOD facial | 14 gsm 2 ply HYPOD treated facial tissue | 16.8 | 1176 |
| Control (UCTAD) | 43 gsm 1 ply UCTAD | 0 | 0 |
| HYPOD UCTAD | 43 gsm 1 ply HYPOD treated UCTAD | 2.6 | 1118 |

Refer to Table 1 for additional code information

Sensory Panel Results: Two separate sensory panel studies were conducted: one for the facial tissue product of the present invention and the other for the UCTAD bath tissue. The softness results are listed in Tables 10 and 11.

TABLE 10

| Code | Overall Probability | Log Odds | Standard Error | 95% Grouping |
|---|---|---|---|---|
| HYPOD Facial Tissue | 91.7 | 0.0000 | 0.6030 | A |
| Control Facial Tissue | 8.3 | −2.3978 | 0.6030 | B |

TABLE 11

| Code | Overall Probability | Log Odds | Standard Error | 95% Grouping |
|---|---|---|---|---|
| UCTAD Tissue With HYPOD | 94.4 | 0.0000 | 0.7276 | A |
| UCTAD Control | 5.6 | −2.8332 | 0.7276 | B |

The results show that the surface treatment of the present invention improved tissue softness by the log odds of 2, meaning that it feels 100 times softer. Both HYPOD treated facial and UCTAD tissues performed better than their respective controls with a 95% confidence.

Study II:

Tissue Product Codes: Six tissue materials were selected from Example 5 and converted into 2-ply facial tissues. Both sides of the tissues were treated and faced outward. Table 12 summarizes the six codes with HYPOD add-on data. The tissue content of HYPOD was determined by measuring the potassium content of the tissue samples versus the HYPOD dry polymer potassium content. (The HYPOD PRIMACOR component is potassium polyacrylate).

TABLE 12

| | | HYPOD Content | |
|---|---|---|---|
| Code | Description | (%) | mg/m² |
| Standard facial tissue Control | 14 gsm 2 ply facial tissue converted from Code 1 of Example 5 | 0 | 0 |
| SAP facial tissue Control | 14 gsm 2 ply facial tissue converted from Code 2 of Example 5 | 0 | 0 |
| SFK tissue Control | 14 gsm 2 ply facial tissue converted from Code 3 of Example 5 | 0 | 0 |
| Standard Pictou | 14 gsm 2 ply facial tissue converted from Code 8 of Example 5 | 2.75 | 195 |
| HYPODSAP | 14 gsm 2 ply facial tissue converted from Code 8 of Example 5 | 3.07 | 218 |
| HYPOD SFK | 14 gsm 2 ply facial tissue converted from Code 9 of Example 5 | 2.47 | 176 |

SFK is 100% recycle fiber upgrade from SFK

Sensory Panel Results are listed in Table 13:

TABLE 13

| Code | Overall Probability | Log Odds | Standard Error | 95% Grouping |
|---|---|---|---|---|
| Mainline | 54.1 | 1.6920 | 0.4106 | A |
| SAP | 34.1 | 1.2258 | 0.4439 | A |
| SFK | 9.9 | 0.0000 | 0.5326 | B |
| Mainline Control | 1.2 | −2.2185 | 0.5069 | C |
| SAP Control | 0.7 | −3.0225 | 0.5744 | C |
| SFK Control | 0.0 | −6.3712 | 0.7762 | E |

Example 8

In this example, additive compositions were either frothed or diluted before they were applied to the Yankee dryer. The application of the additive compositions was done in-line with a froth applicator or a spraying boom. The froth applicator applied the additive chemistry to a Yankee dryer at a solid level of 20 wt %, and the liquid spraying boom (known in the prior art) applied the additive chemistry to a Yankee dryer at a less than 1 wt % solid level. (The Yankee dryer on which the film was formed had a diameter of 61 cm (24 inches).) The additive chemistry was heated and thus formed a film structure.

The wet sheets were dried on the hot Yankee dryer surface together with the additive chemistry (now a film), applied to the dryer as a frothed or sprayed HYPOD. Using a pressure roll, the film was directly bonded to the dried wet cellulose-pulp sheets containing about 40% solids by weight. (The pulps used for these two codes were Eucalyptus and Pictou fiber (Northern soft wood kraft). The coated tissue was then creped by scraping the tissue off of the dryer surface.

Code 1 was the product produced by with the frothed HYPOD surface treatment of the present invention, while Sample 2 was produced with the sprayed HYPOD surface treatment. Code 2 was used as a control of current facial tissue manufacturing technology. The amount of additive chemistries applied to the tissues was about the same for both codes. The additive ("coating") composition data in Table 14 indicates that they were substantially close, with the sprayed code slightly higher. The two codes were both surface treated by the same additive chemistry by using the two different methods of application. Any difference of softness between the two codes (per the IHR test), is due to the very different structure of the additive composition as applied to the samples. See FIG. 6.

TABLE 14

| Facial Tissue Code | Coating Composition (g/10 kg dispersion)* | | Spraying Settings | | Foam Unit Settings | | | Tissue GMT (gf) |
|---|---|---|---|---|---|---|---|---|
| | HYPOD | Na₂CO₃ | No. of Tips | Boom Press. (psi) | Flow Rate (ml/min) | Mixing (%) | Blow Ratio | |
| 1 | 4760 | 2 | NA | NA | 100 | 30 | 6 | 900 |
| | 70% Euc/ 30% Pictou | | | | | | | |
| 2 | 233 | 2 | 3 | 100 | NA | NA | NA | 756 |
| | 70% Euc/ 30% Pictou | | | | | | | |

| Code | Process Parameter | | |
|---|---|---|---|
| | Sheet Temp (°F.) | Machine Speed (ft/min) | HYPOD Add-on (mg/m²) |
| 1 | 257 | 60 | 1270 |
| 2 | 250 | 60 | 1453 |

Study III:

Tissue Product Codes: Two tissue materials were selected from Example 8 and converted into facial tissue products. The resulting facial tissue after was a 2-ply product with the treated side facing outward. Therefore, each surface of the facial tissues was treated.

Sensory Panel Results: A sensory panel study was conducted on these two facial tissues. The softness results are listed in Tables 15. The results indicate that the facial tissue with the frothed HYPOD surface treatment is significantly softer than the tissue having the sprayed HYPOD surface treatment.

TABLE 15

| Code | Overall Probability | Log Odds | Standard Error | 95% Grouping |
|---|---|---|---|---|
| Code 1 from Table 14 | 65.8 | 0.0000 | 0.5127 | A |
| Code 2 from Table 14 | 13.5 | −1.585 | 0.3944 | B |

Example 9

In this example, additive compositions and enhancement components were mixed in a container with a powerful stirrer and then diluted to the designed solids level. When the enhancement components were added into the additive compositions, it was important to make sure that the enhancement components dispersed uniformly under sufficient amount of agitation. The benefit agents (mixed additive compositions and enhancement components) were then pumped into a Gaston foam unit and frothed before they were applied to the Yankee dryer. The application of the benefit agent was done in-line with a froth applicator. The control code, made with a conventional creping chemistry solution (refer to Example 5 Code 1) was applied onto the Yankee dryer by a spraying boom at a less than 1 wt. % solid level. (The Yankee dryer on which the film was formed for either benefit agent or conventional creping chemistry solution had a diameter of 61 cm (24 inches).) Both types of the liquids were heated by the dryer and thus formed a film structure on the surface of the dryer.

(The pulps used for these two codes were Eucalyptus and Pictou fiber (Northern soft wood kraft with Eucalyptus on outer layers and Pictou fiber in middle layer as described in Example 5 Code 1). Using a pressure roll, the benefit agent film (or conventional creping film) was directly bonded to the wet cellulose-pulp sheets containing about 40% solids by weight. The wet pulp sheets were dried on the hot Yankee dryer surface together with the benefit agents or the sprayed conventional creping chemistry. The coated tissue was then creped by scraping the tissue off of the dryer surface with a blade.

Control Code 901 was the product produced with the sprayed conventional creping chemistry solution, while Code 902 was produced with the frothed additive composition HYPOD® surface treatment of the present invention. However, the benefit agents for Code 902 only comprised an additive composition. Codes 904 to 912 were the products produced with the frothed benefit agents comprising both additive composition and enhancement components. Code 904 had 6 wt. % poly(1-vinylpyrrolidone-styrene) dispersion (PVS), available from Aldrich, Milwaukee, Wis., as its enhancement component, while Code 905 had 10 wt. % PVS. Code 906 had 6 wt. % solid silica gel particles (SG) with a particle size from 9.5 to 11 microns, also available from Aldrich, Milwaukee, Wis., and Code 907 had 3 wt. % cotton linter flocks (CLF) with a fiber length around 0.35 mm, commercially available from International Fiber Corp., North Tonawanda, N.Y. Code 910 had 6 wt. % Expancel® expandable microspheres (EXP) 909 DUX 80, commercially available from AkzoNobel, Duluth, Ga., as its enhancement component, while Code 912 had two enhancement components: 3 wt % CLF and 6 wt. % EXP.

Table 16 below summarizes the code list, compositions of the benefit agents used, frothing conditions and detailed production conditions and GMT of the tissues produced.

TABLE 16

| Code | Additive Composition | Benefit Agents Enhancement Component 1* | Benefit Agents Enhancement Component 2* | Foam Unit Parameter Flow Rate (ml/min) | Foam Unit Parameter Mixing (rpm) | Foam Unit Parameter Blow Ratio |
|---|---|---|---|---|---|---|
| 901 | Conventional creping chemistry solution applied not by a froth process** | | | | | |
| 902 | 20% HYPOD 8510 | 0% | 0% | 200 | 180 | 12 |
| 904 | 20% HYPOD 8510 | 6% PVS | 0% | 150 | 180 | 12 |
| 905 | 20% HYPOD 8510 | 10% PVS | 0% | 150 | 180 | 12 |
| 906 | 20% HYPOD 8510 | 6% SG | 0% | 150 | 180 | 12 |
| 907 | 20% HYPOD 8510 | 3% CLF | 0% | 150 | 180 | 12 |
| 908 | 20% HYPOD 8510 | 1% EXP | 0% | 150 | 180 | 12 |
| 909 | 20% HYPOD 8510 | 3% EXP | 0% | 150 | 180 | 12 |
| 910 | 20% HYPOD 8510 | 6% EXP | 0% | 150 | 180 | 12 |
| 912 | 20% HYPOD 8510 | 3% CLF | 6% EXP | 125 | 180 | 12 |

| Code | Machine Parameter Sheet Temp. (° F.) | Machine Parameter Line Speed (fpm) | Machine Parameter Tissue GMT*** (gf) |
|---|---|---|---|
| 901 | 235 | 50 | 905 |
| 902 | 257 | 50 | 1050 |
| 904 | 258 | 50 | 1042 |
| 905 | 258 | 50 | 1088 |
| 906 | 259 | 50 | 1072 |
| 907 | 259 | 50 | 980 |
| 908 | 260 | 50 | 954 |
| 909 | 262 | 50 | 945 |
| 910 | 259 | 50 | 1006 |
| 912 | 260 | 50 | 940 |

Note:
*Enhancement component percentage is calculated based on dry weight of the additive composition;
**Conventional water soluble polymer creping chemistry for facial tissue production applied through a spraying boom underneath Yankee dryer;
***This GMT was measured on un-converted tissue sheet compared to the GMT values in FIG. 12 that were measured on the 2 ply facial tissue product after conversion.

Example 10

In Table 17, 13 different dry substrates were selected and surface coated with different benefit agents with different combinations of additive compositions and enhancement components to achieve softness improvement. These substrates are: (1) 8 to 20 gsm polypropylene spunbond materials; (2) 20 gsm disposable training pant outer cover material; (3) 16 gsm Texol film; (4) 24 gsm aperture nonwoven material (5) 35 gsm coform/spunbond/coform laminate material; (6) 68 gsm 351H Intrepid® filtration media, a fabric for air filters at the MERV 8 level; (7) 54 gsm Hydroknit® basesheet; (8) 20 gsm diaper outer cover material; (9) 12 gsm SMS material; (10) 25 gsm BCW material; and (11) 40 gsm coform material comprising 45% Vistmaxx and 55% wood pulp. All of the dry substrates were treated in an offline creping process.

A commercial HYPOD 8510® dispersion or an experiment polyolefin dispersion was mixed separately with different types of enhancement components in a container by a powerful stirrer and then diluted to the designed solids levels. The experiment polyolefin dispersion (DPOD 80/20) is an experimental dispersion provided by Dow Chemical which comprises a 80 wt. % AFFINITY® and 20 wt. % PRIMACOR®, has a solid level of 55 wt. %, and exhibits a viscosity of around 1,200 cps. When the enhancement components were added into the additive compositions, it was important to make sure that the enhancement components dispersed uniformly under sufficient amount of agitation. The mixed additive compositions and enhancement components (benefit agents) were then pumped into a Gaston foam unit and frothed before they were applied to a hot calender dryer. The application of the benefit agent was done off-line with a froth applicator. In the off-line application, the benefit agent froth was applied onto hot surface of the dryer and then directly bonded with the dry substrate by a pressure roll. In comparison to the in-line application, the substrates used are dry and contain no water. Therefore, the requirement of heating capacity for the dryer is much less for the off-line application process.

The treated substrate was then scraped off the hot calender dryer surface after the froth was cured. The hot calender dryer had a diameter of 19.5 inches and heated to a temperature range of between 240° F. and 330° F. for sufficient curing of the benefit agents. Selection of the dryer's temperature was also related to type of a substrate material. When the substrate is over-heated, it tends to become stiff and brittle due to formation of too many interfiber bonds which will defeat the purpose of this surface treatment.

All of the treated substrates listed in Table 17 exhibited significant improvement in overall softness and surface hand feel in comparison to its untreated controls.

TABLE 17

| | Substrate | | | | Foam Unit Settings | | |
|---|---|---|---|---|---|---|---|
| | | Basis | Benefit Agents | | Flow | | |
| Code | Description | Weight (gsm) | Additive Composition | Enhancement Component | Rate (ml/min) | Mixing (%) | Blow Ratio |
| 241 | Spunbond | 8 | 30% HYPOD | 10% EXP | 50 | 30 | 12 |
| 242 | Spunbond | 12 | 30% HYPOD | 10% SG | 100 | 30 | 10 |
| 244 | Training Pant Outer Cover | 20 | 30% HYPOD | 10% SG | 100 | 30 | 8 |
| 490 | Texol w/o vendor surfactant | 16 | 30% HYPOD | 10% EXP | 150 | 30 | 11 |
| 496 | PP Spunbond | 20 | 30% HYPOD | 10% SG | 200 | 30 | 9 |
| 497 | Apertured Nonwoven | 24 | 30% HYPOD | 10% SG | 200 | 30 | 9 |
| 498 | Spunbond | 20 | 30% HYPOD | 10% SG | 200 | 30 | 9 |
| 507 | Coform/SB/Coform Laminate 351H | 35 | 30% HYPOD | 10% EXP | 175 | 40 | 13 |
| 510 | Intrepid ® Filtration Media | 68 | 30% HYPOD | 10% EXP | 250 | 40 | 13 |
| 511 | Hydroknit ® Basesheet | 54 | 30% HYPOD | 10% EXP | 100 | 40 | 13 |
| 513 | Outer Cover | 20 | 30% HYPOD | 10% EXP | 150 | 30 | 13 |
| 615 | SMS | 12 | 30% DPOD 80/20 | 5% EXP | 300 | 60 | 8 |
| 616 | Spunbond | 8 | 30% DPOD 80/20 | 5% SG | 200 | 70 | 6 |
| 1102 | BCW | 24 | 30% HYPOD | 6% SG | 251 | 50 | 8 |
| 1103 | Coform (Vistmaxx/pulp = 45/55) | 40 | 30% HYPOD | 6% SG | 222 | 50 | 8 |

| | Process Parameters | |
|---|---|---|
| Code | Dryer Temp. (° F.) | Machine Speed (ft/min) |
| 241 | 290 | 50 |
| 242 | 290 | 50 |
| 244 | 248 | 50 |
| 490 | 260 | 50 |
| 496 | 260 | 50 |
| 497 | 260 | 50 |
| 498 | 260 | 50 |
| 507 | 260 | 50 |
| 510 | 280 | 50 |
| 511 | 280 | 50 |
| 513 | 280 | 50 |
| 615 | 250 | 50 |
| 616 | 270 | 50 |

TABLE 17-continued

| 1102 | 325 | 50 |
| 1103 | 325 | 50 |

Test Methods (1) In-Hand Ranking Test for Tactile Properties (IHR Test):

The In-Hand Ranking Test (IHR) is a basic assessment of in-hand feel of fibrous webs and assesses attributes such as softness. This test is useful in obtaining a quick read as to whether a process change is humanly detectable and/or affects the softness perception, as compared to a control. The difference of the IHR softness data between a treated web and a control web reflects the degree of softness improvement.

A panel of testers was trained to provide assessments more accurately than an average untrained consumer might provide. Rank data generated for each sample code by the panel were analyzed using a proportional hazards regression model. This model computationally assumes that the panelist proceeds through the ranking procedure from most of the attribute being assessed to least of the attribute. The softness test results are presented as log odds values. The log odds are the natural logarithm of the risk ratios that are estimated for each code from the proportional hazards regression model. Larger log odds indicate the attribute of interest is perceived with greater intensity.

Because the IHR results are expressed in log odds, the difference in improved softness is actually much more significant than the data indicates. For example, when the difference of IHR data is 1, it actually represents 10 times ($10^1=10$) improvement in overall softness, or 1,000% improvement over its control. In another example, if the difference is 0.2, it represents 1.58 times ($10^{0.2}=1.58$) or a 58% improvement.

The data from the IHR can also be presented in rank format. The data can generally be used to make relative comparisons within tests as a product's ranking is dependent upon the products with which it is ranked. Across-test comparisons can be made when at least one product is tested in both tests.

(2) Sheet Bulk Test

Sheet bulk is calculated as the quotient of the sheet caliper of a conditioned fibrous sheet, expressed in microns, divided by the conditioned basis weight, and expressed in grams per square meter. The resulting sheet bulk is expressed in cubic centimeters per gram. More specifically, the sheet caliper is the representative thickness of a single sheet measured in accordance with TAPPI test methods T402 "Standard Conditioning and Testing Atmosphere For Paper, Board, Pulp Handsheets and Related Products" and T411 om-89 "Thickness (caliper) of Paper, Paperboard, and Combined Board" with Note 3 for stacked sheets. The micrometer used for carrying out T411 om-89 is an Emveco 200-A Tissue Caliper Tester available from Emveco, Inc., Newberg, Oreg., U.S.A. The micrometer has a load of 2 kilo-Pascals, a pressure foot area of 2500 square millimeters, a pressure foot diameter of 56.42 millimeters, a dwell time of 3 seconds and a lowering rate of 0.8 millimeters per second.

(3) Viscosity Test

Viscosity is measured using a Brookfield Viscometer, model RVDV-II+, available from Brookfield Engineering Laboratories, Middleboro, Mass., U.S.A. Measurements are taken at room temperature (23 C), at 100 rpm, with either spindle 4 or spindle 6, depending on the expected viscosity. Viscosity measurements are reported in units of centipoise.

(4) Quantity of HYPOD 8510® Additive Composition Test

In one aspect of the invention, HYPOD add-on is determined by using acid digestion. Samples are wet ashed with enough concentrated sulfuric and nitric acid to destroy the carbonaceous material and isolate the potassium ions from the cellulosic matrix. The potassium concentration is then measured by atomic absorption. HYPOD 8510® add-ons are determined by referencing the potassium concentration of the HYPOD 8510® on the sample to bulk HYPOD 8510® measurements from a control HYPOD 8510® dispersion solution (LOTVB1955WC30, 3.53%).

(5) Method for Determining Content of Additive Composition in Tissue.

Samples were digested following EPA method 3010A. The method consists of digesting a known amount of material with Nitric Acid in a block digester and bringing it up to a known volume at the end of the digestion.

Analysis was performed on a flame atomic absorption spectrophotometer using EPA method 7610 dated July 1986, which is a direct aspiration method using an air/acetylene flame. The instrument used was a VARIAN AA240FS available from Aligent Technologies, Santa Clara, Calif., U.S.A.

The analysis was performed in the following manner: The instrument was calibrated with a blank and five standards. Calibration was followed with analyzing a second source standard to confirm the calibration standards. In this particular case, recovery was 97% (90-110% being acceptable). Next a digestion blank and a digestion standard were analyzed. In this particular case, the blank was less than 0.1 mg/l and the standard recovery was 93% (85-115% being acceptable). Samples were then analyzed and after every tenth sample a standard was run (90-110% being acceptable). At the end of entire analysis, a blank and standard were run.

(6) Basis Weight

The Basis Weight of the tissue sheet specimens was determined using a modified TAPPI T410 procedure. The pre-plied samples were conditioned at 23° C.±1° C. and 50±2% relative humidity for a minimum of 4 hours. After conditioning a stack of 16-3"×3" pre-plied samples was cut using a die press and associated die. This represents a tissue sheet sample area of 144 in$^2$ or 0.0929 m$^2$. Examples of suitable die presses are TMI DGD die press manufactured by Testing Machines, Inc. located at Islandia, N.Y., or a Swing Beam testing machine manufactured by USM Corporation, located at Wilmington, Mass. Die size tolerances are +/−0.008 inches in both directions. The specimen stack is then weighed to the nearest 0.001 gram on a tared analytical balance. The basis weight in grams per square meter (gsm) is calculated using the following equation:

Basis weight (conditioned)=stack wt. in grams/(0.0929 m$^2$)

(7) Geometric Mean Tensile Strength (GMT)

The Geometric Mean Tensile Strength (GMT) is the square root of the product of the dry machine direction (MD) tensile strength multiplied by the dry cross-machine direction (CD) tensile strength and is expressed as grams per 3 inches of sample width. The MD tensile strength is the peak load per 3 inches of sample width when a sample is pulled to rupture in the machine direction. Similarly, the CD tensile strength is the peak load per 3 inches of sample width when a sample is pulled to rupture in the cross-machine direction. The tensile curves are obtained under laboratory conditions of 23.0° C.±1.0° C., 50.0±2.0% relative humidity and after the tissue samples have equilibrated to the testing conditions for a period of not less than four hours.

The samples for tensile strength testing are cut into strips 3 inches wide (76 mm) by at least 5 inches (127 mm) long in either the machine direction (MD) or cross-machine direction (CD) orientation using a JDC Precision Sample Cutter (Thwing-Albert Instrument Company, Philadelphia, Pa., Model No. SC130). The tensile tests are measured on an MTS Systems Synergie 100 run with TestWorks® 4 software version 4.08 (MTS Systems Corp., Eden Prairie, Minn.).

The load cell is selected from either a 50 Newton or 100 Newton maximum, depending on the strength of the sample being tested, such that the majority of peak load values fall between 10-90% of the load cell's full scale value. The gauge length between jaws is 4+/−0.04 inches (102+/−1 mm). The jaws are operated using pneumatic-action and are rubber coated. The minimum grip face width is 3 inches (76 mm), and the approximate height of a jaw is 0.5 inches (13 m). The crosshead speed is 10+/−0.4 inches/min (254+/−10 mm/min), and the break sensitivity is set at 65%.

The sample is placed in the jaws of the instrument, centered both vertically and horizontally. The test is then started and ends when the specimen breaks. The peak load is recorded as either the "MD tensile strength" or the "CD tensile strength" of the specimen depending on direction of the sample being tested. Ten (10) specimens per sample are tested in each direction with the arithmetic average being reported as either the MD or CD tensile strength value for the product. The geometric mean tensile strength is calculated from the following equation:

$$GMT = (MD\ Tensile * CD\ Tensile)^{1/2}$$

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

All documents cited in the Detailed Description of the Invention are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by reference, the meaning or definition assigned to the term in this written document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method of creping a nonwoven substrate comprising the steps of:
   a) providing a nonwoven substrate;
   b) positioning an applicator adjacent to a hot, non-permeable drying surface;
   c) through said applicator, applying to the drying surface an aqueous, frothed, benefit agent wherein said benefit agent comprises an additive composition;
   d) allowing the frothed, benefit agent to form an adhesive film onto the drying surface, the adhesive film having air bubbles therein;
   e) directly bonding the nonwoven substrate to the adhesive film positioned on the drying surface; and
   f) scraping the bonded nonwoven substrate and adhesive film from the drying surface.

2. The method of claim 1 wherein the additive composition comprises a mixture of a synthetic water-soluble polymer and a natural water-soluble polymer.

3. The method of claim 1 wherein the additive composition is a polymer dispersion selected from the group consisting of polyolefin dispersions, polybutadiene-styrene block copolymer dispersions, latex pyrrolidone-styrene copolymer dispersions, polyvinyl alcohol-ethylene copolymer dispersions, and combinations thereof.

4. The method of claim 1 wherein the benefit agent further comprises an enhancement component.

5. The method of claim 4 wherein said enhancement component is selected from the group consisting of micro-particles, thermally expandable microspheres, cut fibers, additional polymer dispersions, fragrances, anti-bacterials, moisturizers, soothers, medicaments and combinations thereof.

6. The method of claim 1 wherein the nonwoven substrate is a tissue and exhibits increased softness according to the In-Hand Ranking Test for Tactile Properties by a log odds of from about 0.5 to about 18, and a GMT level of from about 800 to about 1200.

* * * * *